United States Patent [19]

Pirotte et al.

[11] Patent Number: 5,792,764
[45] Date of Patent: Aug. 11, 1998

[54] PYRIDO-1,2,4-THIADIAZINE AND PYRIDO-1, 4-THIAZINE DERIVATIVES, THEIR PREPARATION AND USE

[75] Inventors: Bernard Pirotte, Oupeye; Philippe Lebrun, Brussels; Pascal De Tullio; Fabian Somers, both of Liege; Jacques Delarge, Dolembreux, all of Belgium; Holger Claus Hansen, Værløse, Denmark; Flemming Elmelund Nielsen, Virum, Denmark; John Bondo Hansen, Jyderup, Denmark

[73] Assignee: Novo Nordisk A/S, Bagsvaerd, Denmark

[21] Appl. No.: 785,435

[22] Filed: Jan. 17, 1997

[30] Foreign Application Priority Data

| Jan. 17, 1996 | [DK] | Denmark | 0042/96 |
| Mar. 5, 1996 | [DK] | Denmark | 0246/96 |
| Mar. 5, 1996 | [DK] | Denmark | 0247/96 |
| Mar. 5, 1996 | [DK] | Denmark | 0248/96 |
| Mar. 5, 1996 | [DK] | Denmark | 0249/96 |

[51] Int. Cl.$^6$ .................. C07D 513/04; A61K 31/54
[52] U.S. Cl. .................. 514/222.8; 544/10; 544/48; 514/224.2
[58] Field of Search .................. 544/10; 514/222.8

[56] References Cited

U.S. PATENT DOCUMENTS 5,459,138  10/1995  Pirotte et al. .................. 514/222.8

FOREIGN PATENT DOCUMENTS

0618209 A1  10/1994  European Pat. Off. .
1368948  10/1974  United Kingdom .

OTHER PUBLICATIONS

Pirotte, B., et al., Biochemical Pharma., vol. 47, No. 8, pp. 1381–1386, 1994.

Pirotte, B., et al., J. Med. Chem., vol. 36, pp. 3211–3213, 1993.

Dupont, L., et al., Acta Cryst., vol. C51, pp. 1903–1905, 1995.

Vlahos, W.D., et al., Metabolism, vol. 40, No. 8, pp. 825–829, 1991.

*Primary Examiner*—Matthew V. Grumbling
*Attorney, Agent, or Firm*—Steve T. Zelson; Cheryl Agris

[57] ABSTRACT

Pyrido-1,2,4-thiadiazine and pyrido-1,4-thiazine derivatives represented by the formula

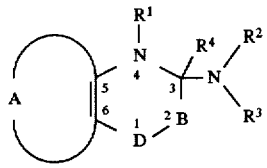

wherein A, B, D, $R^1$, $R^2$, $R^3$ and $R^4$ are defined in the description, compositions thereof and methods for preparing the compounds are described. The compounds are useful in the treatment of diseases of the central nervous system, the cardiovascular system, pulmonary system, the gastrointestinal system and the endocrinologic system.

52 Claims, No Drawings

1

PYRIDO-1,2,4-THIADIAZINE AND PYRIDO-1,4-THIAZINE DERIVATIVES, THEIR PREPARATION AND USE

CROSS-REFERENCE TO RELATED APPLICATIONS

This application claims priority under 35 U.S.C. 119 of Danish applications 0042/96 filed 17 Jan. 1996, 0246/96 filed 5 Mar. 1996, 0247/96 filed 5 Mar. 1996, 0248/96 filed 5 Mar. 1996, 0249/96 filed 5 Mar. 1996, the contents of which applications are fully incorporated herein by reference.

FIELD OF THE INVENTION

The present invention relates to pyrido-1,2,4-thiadiazine and pyrido-1,4-thiazine derivatives, to methods for their preparation, to compositions comprising the compounds, to the use of these compounds as medicaments and their use in therapy e.g. in the treatment of diseases of the central nervous system, the cardiovascular system, the pulmonary system, the gastrointestinal system and the endocrinological system.

BACKGROUND OF THE INVENTION

Potassium channels play an important role in membrane potential. Among the different types of potassium channels are the ATP-sensitive ($K_{ATP}$-) channels which are regulated by changes in the intracellular concentration of adenosine triphosphate. The $K_{ATP}$-channels have been found in cells from various tissues such as cardiac cells, pancreatic-cells, skeletal muscles, smooth muscles, central neurons and adenohypophysis cells. The channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system.

Modulators of the $K_{ATP}$-channels have been found to be of importance for the treatment of various diseases. Certain sulfonylureas which have been used for the treatment of non-insulin-dependent diabetes mellitus act by stimulating insulin release through an inhibition of the $K_{ATP}$-channels on pancreatic beta-cells.

The potassium channel openers, which comprise a heterogeneous group of compounds, have been found to be able to relax vascular smooth muscles and have therefore been used for the treatment of hypertension.

In addition, potassium channel openers can be used as bronchodilators in the treatment of asthma and various other diseases.

Furthermore, potassium channel openers have been shown to promote hairgrowth, and have been used for the treatment of baldness.

Potassium channel openers are also able to relax urinary bladder smooth muscle and therefore, can be used for the treatment of urinary incontinence. Potassium channel openers which relax smooth muscle of the uterus can be used for treatment of premature labor.

By acting on potassium channels of the central nervous system these compounds can be used for treatment of various neurological and psychiatric diseases such as Alzheimer, epilepsia and cerebral ischemia.

Recently, it has been shown that Diazoxide (7-chloro-3-methyl-2H-1,2,4-benzothiadiazine 1,1-dioxide) and certain 3-(alkylamino)-4H-pyrido[4,3-e]-1,2,4-thiadiazine 1,1-dioxide derivatives inhibit insulin release by an activation of $K_{ATP}$-channels on pancreatic beta-cells (Pirotte B. et al. *Biochem. Pharmacol*, 47, 1381–1386 (1994); Pirotte B. et al., *J. Med. Chem.*, 36, 3211–3213 (1993). Diazoxide has furthermore been shown to delay the onset of diabetes in BB-rats (Vlahos WD et al. *Metabolism* 40, 39–46 (1991). In obese zucker rats diazoxide has been shown to decrease insulin secretion and increase insulin receptor binding and consequently improve glucose tolerance and decrease weight gain (Alemzadeh R. et al. *Endocrinol.* 133, 705–712, 1993). It is expected that such compounds can be used for treatment of diseases characterised by an overproduction of insulin and for the treatment and prevention of diabetes.

EP 618 209 discloses a class of pyridothiadiazine derivatives having an alkyl or an alkylamino group in position 3 of the thiadiazine ring. These compounds are claimed to be agonists at the AMPA-glutamate receptor.

In Acta Crystallographica Section C, 1995, C51 (9), 1903–1905 the crystal structure of 3-benzamido-4H-pyrido [4,3-e]-1,2,4-thiadiazine 1,1-dioxide is described.

DESCRIPTION OF THE INVENTION

The present invention relates to pyrido-1,2,4-thiadiazine and pyrido-1,4-thiazine derivatives of the general formula I:

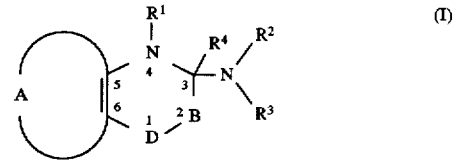

wherein

B represents >$NR^5$ or >$CR^5R^6$, wherein $R^5$ and $R^6$ independently can be hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen; or $R^5$ and $R^4$ together represent one of the bonds in a double bond between the atom 2 and 3 of formula I;

D represents —S(=O)$_2$— or —S(=O)—; or

D-B represents—S(=O)($R^{10}$)=N— wherein $R^{10}$ is $C_{1-6}$-alkyl; or aryl or heteroaryl optionally mono- or polysubstituted with halogen, hydroxy, $C_{1-6}$-alkoxy, aryloxy, arylalkoxy, nitro, amino, $C_{1-6}$-monoalkyl- or dialkylamino, cyano, acyl, or $C_{1-6}$-alkoxycarbonyl;

$R^1$ is hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen or $R^4$ together with $R^5$ represent one of the bonds in a double bond between the atoms 2 and 3 of formula I; or $R^1$ together with $R^4$ represent one of the bonds in a double bond between the atoms 3 and 4 of formula I;

$R^2$ is hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen;

$R^3$ is $R^{11}$; —$OR^{11}$; —C(=x)$R^{11}$; —$NR^{11}R^{12}$; bicycloalkyl, aryl, heteroaryl, arylalkyl or heteroarylalkyl optionally mono- or polysubstituted with halogen, hydroxy, $C_{1-6}$-alkoxy, aryloxy, arylalkoxy, nitro, amino, $C_{1-6}$-monoalkyl- or dialkylamino, cyano, oxo, acyl or $C_{1-6}$-alkoxycarbonyl; or aryl substituted with $C_{1-6}$-alkyl;

wherein $R^{11}$ is hydrogen; $C_{3-6}$-cycloalkyl or $(C_{3-6}$-cycloalkyl)$C_{1-6}$-alkyl, the $C_{3-6}$-cycloalkyl group optionally being mono- or polysubstituted with $C_{1-6}$-alkyl, halogen, hydroxy or $C_{1-6}$-alkoxy; a 3-6 membered saturated ring system comprising one or more nitrogen-, oxygen- or sulfur atoms; or straight or branched $C_{1-18}$-alkyl optionally mono- or polysubstituted with halogen, hydroxy, $C_{1-6}$-alkoxy, $C_{1-6}$-alkylthio, $C_{3-6}$-cycloalkyl, aryl, aryloxy, arylalkoxy, nitro, amino, $C_{1-6}$-monoalkyl- or dialkylamino, cyano, oxo, formyl, acyl, carboxy, $C_{1-6}$-alkoxycarbonyl, or carbamoyl;

X is O or S;

$R^{12}$ is hydrogen; $C_{1-6}$-alkyl; $C_{2-6}$-alkenyl; $C_{3-6}$-cycloalkyl optionally mono- or polysubstituted with $C_{1-6}$-alkyl, halogen, hydroxy or $C_{1-6}$-alkoxy or $R^{11}$ and $R^{12}$ together with the nitrogen atom form a 3-12 membered mono- or bicyclic system, in which one or more of the carbon atoms may be exchanged with nitrogen, oxygen or sulfur, each of these ring systems optionally being mono- or polysubstituted with halogen, $C_{1-6}$-alkyl, hydroxy, $C_{1-6}$-alkoxy, $C_{1-6}$-alkoxy-$C_{1-6}$-alkyl, nitro, amino, cyano, trifluoromethyl, $C_{1-6}$-monoalkyl- or dialkylamino, oxo; or $R^3$ is

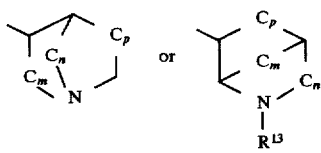

wherein n,m,p independently are 0,1,2,3 and $R^{13}$ is hydrogen; hydroxy; $C_{1-6}$-alkoxy; $C_{3-6}$-cycloalkyl optionally mono- or polysubstituted with $C_{1-6}$-alkyl, halogen, hydroxy or $C_{1-6}$-alkoxy; $C_{1-6}$-alkyl, $C_{2-6}$-alkenyl or $C_{2-6}$-alkynyl optionally mono- or polysubstituted with halogen;

or $R^2$ and $R^3$ together with the nitrogen atom form a 3-12 membered mono- or bicyclic system, in which one or more of the carbon atoms may be exchanged with nitrogen, oxygen or sulfur, each of these ring systems optionally being mono- or polysubstituted with halogen, $C_{1-6}$-alkyl, hydroxy, $C_{1-6}$-alkoxy, $C_{1-6}$-alkoxy-$C_{1-6}$-alkyl, nitro, amino, cyano, trifluoromethyl, $C_{1-6}$-monoalkyl- or dialkylamino or oxo;

A together with carbon atoms 5 and 6 of formula I forms a pyridine ring selected from

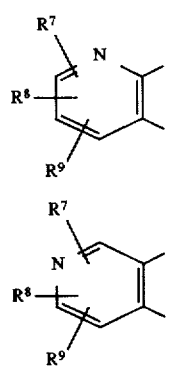

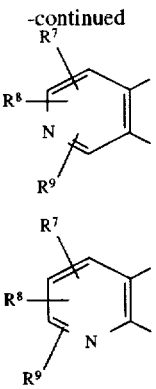

wherein $R^7$, $R^8$, $R^9$ independently are hydrogen; halogen; $C_{1-12}$-alkyl; $C_{3-6}$-cycloalkyl; hydroxy; $C_{1-6}$-alkoxy; $C_{1-6}$-alkoxy-$C_{1-6}$-alkyl; nitro; amino; cyano; cyanomethyl; perhalomethyl; $C_{1-6}$-monoalkyl- or dialkylamino; sulfamoyl; $C_{1-6}$-alkylthio; $C_{1-6}$-alkylsulfonyl; $C_{1-6}$-alkylsulfinyl; $C_{1-6}$-alkylcarbonylamino; arylthio, arylsulfinyl, arylsulfonyl, the aryl group optionally being mono- or polysubstituted with $C_{1-6}$-alkyl, halogen, hydroxy or $C_{1-6}$-alkoxy; $C_{1-6}$-alkoxycarbonyl; $C_{1-6}$-alkoxycarbonyl-$C_{1-6}$-alkyl; carbamyl; carbamylmethyl; $C_{1-6}$-monoalkyl- or dialkylaminocarbonyl; $C_{1-6}$-monoalkyl- or dialkylaminothiocarbo-nyl; ureido; $C_{1-6}$-monoalkyl- or dialkylaminocarbonylamino, thioureido; $C_{1-6}$-monoalkyl- or dialkylami-nothiocarbonylamino; $C_{1-6}$-monoalkyl- or dialkylaminosulfonyl; carboxy; carboxy-$C_{1-6}$-alkyl; acyl; aryl, arylalkyl, aryloxy, the aryl group optionally being mono- or polysubstituted with $C_{1-6}$-alkyl, halogen, hydroxy or $C_{1-6}$-alkoxy; (1,2,4-oxadiazol-5-yl)- or (1,2,4-oxadiazol-3-yl)-$C_{1-6}$-alkyl the oxadiazolyl group optionally being substituted with $C_{1-6}$-alkyl or $C_{3-6}$-cycloalkyl; or a 5-6 membered nitrogen containing ring, optionally substituted with phenyl or $C_{1-6}$-alkyl;

provided that when B represents $NR^5$, D represents $SO_2$ and $R^2$ is hydrogen, $C_{1-6}$-alkyl or $C_{3-6}$-cycloalkyl, then $R^3$ is not hydrogen, unsubstituted $C_{1-6}$-alkyl, $C_{3-6}$-cycloalkyl, $(C_{3-6}$-cycloalkyl)$C_{1-6}$-alkyl, pyrrolidine, piperidine, piperazine, morpholine, thiomorpholine or benzyl, or a salt thereof with a pharmaceutically acceptable acid or base.

Within its scope the invention includes all optical isomers of compounds of formula I, some of which are optically active, and also their mixtures including racemic mixture thereof.

The scope of the invention also includes all tautomeric forms of the compounds of formula I.

The salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methanesulfonic, ethane sulfonic, picric and the like, and include acids related to the pharmaceutically acceptable salts listed in *Journal of Pharmaceutical Science*, 66, 2 (1977) and incorporated herein by reference, or lithium, sodium, potassium, magnesium and the like.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "$C_{1-6}$-alkylthio" as used herein, alone or in combination, refers to a straight or branched monovalent substituent comprising a lower alkyl group linked through a divalent sulfur atom having its free valence bond from the sulfur atom and having 1 to 6 carbon atoms e.g. methylthio, ethylthio, propylthio, butylthio, pentylthio.

The term "$C_{2-6}$-alkenyl" as used herein refers to an unsaturated hydrocarbon chain having 2-6 carbon atoms and one double bond such as e.g. vinyl, 1-propenyl, allyl, isopropenyl, n-butenyl, n-pentenyl and n-hexenyl.

The term "$C_{3-6}$-cycloalkyl" as used herein refers to a radical of a saturated cyclic hydrocarbon with the indicated number of carbons such as cyclopropyl, cyclobutyl, cyclopentyl or cyclohexyl.

The term "$C_{2-6}$-alkynyl" as used herein refers to unsaturated hydrocarbons which contain triple bonds, such as e.g. $-C\equiv CH$, $-C\equiv CCH_3$, $-CH_2C\equiv CH$, $-CH_2CH_2C\equiv CH$, $-CH(CH_3)C\equiv CH$, and the like.

The term "$C_{1-6}$-alkoxy-$C_{1-6}$-alkyl" as used herein refers to a group of 2-12 carbon atoms interrupted by an O such as e.g. $CH_2-O-CH_3$, $CH_2-O-CH_2-CH_3$, $CH_2-O-CH(CH_3)_2$ and the like.

The term "halogen" means fluorine, chlorine, bromine or iodine.

The term "perhalomethyl" means trifluoromethyl, trichloromethyl, tribromomethyl or triiodomethyl.

The terms "$C_{1-6}$-alkyl", "$C_{1-12}$-alkyl" and "$C_{1-18}$-alkyl" as used herein, alone or in combination, refer to a straight or branched, saturated hydrocarbon chain having the indicated number of carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl, 1,2,2-trimethylpropyl and the like. The term "$C_{1-18}$-alkyl" as used herein also includes secondary $C_{3-6}$-alkyl and tertiary $C_{4-6}$-alkyl.

The term "$C_{1-6}$-monoalkylamino" as used herein refers to an amino group wherein one of the hydrogen atoms is substituted with a straight or branched, saturated hydrocarbon chain having the indicated number of carbon atoms such as e.g. methylamino, ethylamino, propylamino, n-butylamino, sec-butylamino, isobutylamino, tert-butylamino, n-pentylamino, 2-methylbutylamino, n-hexylamino, 4-methylpentylamino, neopentylamino, n-hexylamino, 2,2-dimethylpropylamino and the like.

The term "$C_{1-6}$-dialkylamino" as used herein refers to an amino group wherein the two hydrogen atoms independently are substituted with a straight or branched, saturated hydrocarbon chain having he indicated number of carbon atoms; such as dimethylamino, N-ethyl-N-methylamino, diethylamino, ipropylamino, N-(n-butyl)-N-methylamino, di(n-pentyl)amino, and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl, and the like.

The term "$C_{1-6}$-alkoxycarbonyl" as used herein refers to a monovalent substituent comprising a $C_{1-6}$-alkoxy group linked through a carbonyl group; such as e.g. methoxycarbonyl, carbethoxy, propoxycarbonyl, isopropoxycarbonyl, n-butoxycarbonyl, sec-butoxycarbonyl, tert-butoxycarbonyl, 3-methylbutoxycarbonyl, n-hexoxycarbonyl and the like.

The term "3–12 membered mono- or bicyclic system" as used herein refers to a monovalent substituent of formula $-NR^2R^3$ or $-NR^{11}R^{12}$ where $R^2$ and $R^3$, or $R^{11}$ and $R^{12}$ together with the nitrogen atom form a 3–12 membered mono- or bicyclic system, in which one or more of the carbon atoms may be exchanged with nitrogen, oxygen or sulfur, such as 1-pyrrolidyl, piperidino, morpholino, thiomorpholino, 4-methylpiperazin-1-yl, 7-azabicyclo [2.2.1]heptan-7-yl, tropanyl and the like.

The term "3–6 membered saturated ring system" as used herein refers to a monovalent substituent comprising a monocyclic saturated system containing one ore more hetero atoms selected from nitrogen, oxygen and sulfur and having 3–6 members and having its free valence from a carbon atom, e.g. 2-pyrrolidyl, 4-piperidyl, 3-morpholinyl, 1,4-dioxan-2-yl, 5-oxazolidinyl, 4-isoxazolidinyl or 2-thiomorpholinyl.

The term "bicycloalkyl" as used herein refers to a monovalent substituent comprising a bicyclic structure made of 6–12 carbon atoms such as e.g. 2-norbornyl, 7-norbornyl, 2-bicyclo[2.2.2]octyl and 9-bicyclo[3.3.1]nonanyl.

The term "aryl" as used herein refers to phenyl, 1-naphthyl or 2-naphthyl.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine.

The term "arylalkyl" as used herein refers to a straight or branched saturated carbon chain containing from 1 to 6 carbons substituted with an aromatic carbohydride; such as benzyl, phenethyl, 3-phenylpropyl, 1-naphtylmethyl, 2-(1-naphtyl)ethyl and the like.

The term "aryloxy" as used herein refers to phenoxy, 1-naphthyloxy or 2-naphthyloxy.

The term "arylalkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroarylalkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "$C_{1-6}$-alkylsulfonyl" as used herein refers to a monovalent substituent comprising a $C_{1-6}$-alkyl group linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl, n-hexylsulfonyl and 2,2-dimethylpropylsulfonyl.

The term "$C_{1-6}$-monoalkylaminosulfonyl" as used herein refers to a monovalent substituent comprising a $C_{1-6}$-monoalkylamino group linked through a sulfonyl group such as e.g. methylaminosulfonyl, ethylaminosulfonyl, n-propylaminosulfonyl, isopropylaminosulfonyl, n-butylaminosulfonyl, sec-butylaminosulfonyl, isobutylaminosulfonyl, tert-butylaminosulfonyl, n-pentylaminosulfonyl, 2-methylbutylaminosulfonyl, 3-methylbutylaminosulfonyl, n-hexylaminosulfonyl, 4-methylpentylaminosulfonyl, neopentylaminosulfonyl, n-hexylaminosulfonyl and 2,2-dimethylpropylaminosulfonyl.

The term "$C_{1-6}$-dialkylaminosulfonyl" as used herein refers to a monovalent substituent comprising a $C_{1-6}$-dialkylamino group linked through a sulfonyl group such as dimethylaminosulfonyl, N-ethyl-N-methylaminosulfonyl, diethylaminosulfonyl, dipropylaminosulfonyl, N-(n-butyl)-N-methylaminosulfonyl, di(n-pentyl)aminosulfonyl, and the like.

The term "$C_{1-6}$-alkylsulfinyl" as used herein refers to a monovalent substituent comprising a straight or branched $C_{1-6}$-alkyl group linked through a sulfinyl group (—S(=O)—); such as e.g. methylsulfinyl, ethylsulfinyl, isopropylsulfinyl, butylsulfinyl, pentylsulfinyl, and the like.

The term "$C_{1-6}$-alkylcarbonylamino" as used herein refers to an amino group wherein one of the hydrogen atoms is substituted with an acyl group, such as e.g. acetamido, propionamido, isopropylcarbonylamino, and the like.

The term "$(C_{3-6}$-cycloalkyl$)C_{1-6}$-alkyl" as used herein, alone or in combination, refers to a straight or branched, saturated hydrocarbon chain having 1 to 6 carbon atoms and being monosubstituted with a $C_{3-6}$-cycloalkyl group, the cycloalkyl group optionally being mono- or polysubstituted with $C_{1-6}$-alkyl, halogen, hydroxy or $C_{1-6}$-alkoxy; such as e.g. cyclopropylmethyl, (1-methylcyclopropyl)methyl, 1-(cyclopropyl)ethyl, cyclopentylmethyl, cyclohexylmethyl, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)- thio, (2-chlorophenyl)thio, and the like.

The term "arylsulfinyl" as used herein refers to an aryl group linked through a sulfinyl group (—S(=O)—), the aryl group optionally being mono- or polysubstituted with $C_{1-6}$-alkyl, halogen, hydroxy or $C_{1-6}$-alkoxy; such as e.g. phenylsulfinyl, (4-chlorophenyl)sulfinyl, and the like.

The term "arylsulfonyl" as used herein refers to an aryl group linked through a sulfonyl group, the aryl group optionally being mono- or polysubstituted with $C_{1-6}$-alkyl, halogen, hydroxy or $C_{1-6}$-alkoxy; such as e.g. phenylsulfonyl, tosyl, and the like.

The term "$C_{1-6}$-monoalkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpen-tylaminocarbonyl, neopentylaminocarbonyl, n-hexylaminocarbonyl and 2-2-dimethylpropylaminocarbonyl.

The term "$C_{1-6}$-dialkylaminocarbonyl" as used herein refers to a monovalent substituent comprising a $C_{1-6}$-dialkylamino group linked through a carbonyl group such as dimethylaminocarbonyl, N-ethyl-N-methylaminocarbonyl, diethylaminocarbonyl, dipropylaminocarbonyl, N-(n-butyl)-N-methylaminocarbonyl, di(n-pentyl)aminocarbonyl, and the like.

The term "$C_{1-6}$-monoalkylaminocarbonylamino" as used herein refers to an amino group wherein one of the hydrogen atoms is substituted with a $C_{1-6}$-monoalkylaminocarbonyl group, e.g. methylamino-carbonylamino, ethylaminocarbonylamino, n-propylaminocarbonylamino, isopropylaminocarbonylamino, n-butylaminocarbonylamino, sec-butylaminocarbonylamino, isobutylaminocarbonylamino, tert-butylaminocarbonylamino, and 2-methylbutylaminocarbonylamino.

The term "$C_{1-6}$-dialkylaminocarbonylamino" as used herein refers to an amino group wherein one of the hydrogen atoms is substituted with a $C_{1-6}$-dialkylaminocarbonyl group, such as dimethylaminocarbonylamino, N-ethyl-N-methylaminocarbonylamino, diethylaminocarbonylamino, dipropylaminocarbonylamino, N-(n-butyl)-N-methylaminocarbonylamino, di(n-pentyl)aminocarbonylamino, and the like.

The term "5- or 6-membered nitrogen containing ring" as used herein refers to a monovalent substituent comprising a monocyclic unsaturated or saturated system containing one or more nitrogen atoms and having 5 or 6 members, e.g. pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl, 1,3-dioxolanyl and 1,4-dioxolanyl.

Within its scope the invention includes all optical isomers of compounds of formula I, some of which are optically active, and also their mixtures including racemic mixture thereof.

In a preferred embodiment of the invention the general formula of formula I is selected from

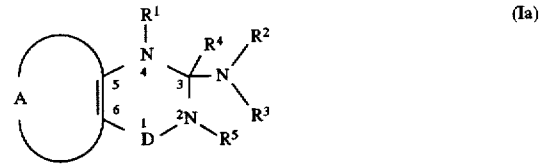
(Ia)

wherein $R^1$ and $R^5$ independently are hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen; or $R^4$ together with $R^5$ represent one of the bonds in a double bond between the atoms 2 and 3 of formula I and $R^1$ is as defined above; or $R^4$ together with $R^1$ represent one of the bonds in a double bond between the atoms 3 and 4 of formula I and $R^5$ is as defined above;

D represents —S(=O)$_2$— or —S(=O)—.

In another preferred embodiment of the invention the general formula of formula I is selected from

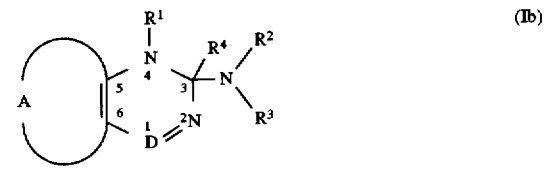
(Ib)

wherein $R^1$ is hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen; or $R^4$ together with $R^1$ represent one of the bonds in a double bond between the atoms 3 and 4 of formula I;

D represents —S(=O)$R^{10}$= wherein $R^{10}$ is $C_{1-6}$-alkyl; aryl or heteroaryl optionally mono- or polysubstituted with halogen, hydroxy, $C_{1-6}$- alkoxy, aryloxy, arylalkoxy, nitro, amino, $C_{1-6}$-monoalkyl- or dialkylamino, cyano, acyl or $C_{1-6}$-alkoxycarbonyl.

In another preferred embodiment of the invention the general formula of formula I is selected from

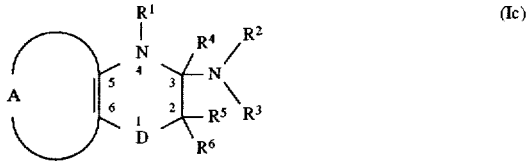

wherein $R^1$, $R^5$ and $R^6$ independently are hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen; or $R^4$ together with $R^5$ represent one of the bonds in a double bond between the atoms 2 and 3 of formula I and $R^1$ and $R^6$ are as defined above; or $R^4$ together with $R^1$ represent one of the bonds in a double bond between the atoms 3 and 4 of formula I and $R^5$ and $R^6$ are as defined above;

D represents —S(=O)$_2$— or S(=O).

Preferably, the general formula of formula I is (Ia).

In another preferred embodiment of the invention D is —S(=O)$_2$—.

In another preferred embodiment of the invention $R^1$ is selected from hydrogen, $C_{1-6}$-alkyl, $C_{3-6}$-cycloalkyl or $C_{2-6}$-alkenyl. Preferably $R^1$ is hydrogen or $C_{1-6}$-alkyl.

In another preferred embodiment of the invention $R^1$ together with $R^4$ represent one of the bonds in a double bond between the atoms 3 and 4 of formula I.

In another preferred embodiment of the invention $R^4$ together with $R^5$ represent one of the bonds in a double bond between the atoms 2 and 3 of formula I.

In another preferred embodiment of the invention $R^2$ is selected from hydrogen, hydroxy, $C_{1-6}$-alkyl, $C_{3-6}$-cycloalkyl or $C_{2-6}$-alkenyl.

In another preferred embodiment of the invention $R^3$ is selected from $R^{11}$, —OR$^{11}$, —NR$^{11}$R$^{12}$ or aryl, the aryl group optionally being substituted with $C_{1-6}$-alkyl; wherein $R^{11}$ is hydrogen; $C_{3-6}$-cycloalkyl; ($C_{3-6}$-cycloalkyl)$C_{1-6}$-alkyl; a 3-6 membered saturated ring system comprising one, two or three nitrogen-, oxygen- or sulfur atoms; or straight or branched $C_{1-18}$-alkyl optionally substituted with halogen, hydroxy, $C_{1-6}$-alkoxy, $C_{1-6}$-alkylthio, $C_{3-6}$-cycloalkyl or aryl; $R^{12}$ is hydrogen, $C_{1-6}$-alkyl or $C_{3-6}$-cycloalkyl; or $R^{11}$ and $R^{12}$ together with the nitrogen atom form a 4-6 membered ring, preferably 1-pyrrolidyl, piperidine or morpholino.

In yet another preferred embodiment of the invention $R^3$ is selected from secondary $C_{3-6}$-alkyl, tertiary $C_{4-6}$-alkyl, $C_{3-6}$-cycloalkyl or ($C_{3-6}$-cycloalkyl)methyl optionally mono- or polysubstituted with $C_{1-6}$-alkyl, halogen, hydroxy or $C_{1-6}$-alkoxy. Preferably $R^3$ is selected from isopropyl, 1-methylpropyl, 2-methylpropyl, tert-butyl, 1,1-dimethylpropyl, 1,2-dimethylpropyl, 1,2,2-trimethylpropyl, 2,3-dimethylbutyl, 1-ethylpropyl, 1-ethyl-2-methylpropyl, 1-ethyl-2,2-dimethylpropyl, 2,3,3-trimethylbutyl, 2-methylbutyl, cyclopropyl, 1-methylcyclopropyl, cyclobutyl, cyclopentyl, cyclohexyl, cyclopropylmethyl, 1-(cyclopropyl)ethyl cyclobutyl-methyl, cyclopentylmethyl or cyclohexylmethyl.

In a further preferred embodiment of the invention $R^2$ and $R^3$ together with the nitrogen atom forms a six membered ring, optionally substituted in the 2-position with a $C_{1-6}$-alkyl group, preferably selected from methyl, ethyl or isopropyl. Preferably the six membered ring is a piperidine, piperazine, morpholine or thiomorpholine ring.

In another preferred embodiment of the invention $R^{10}$ is selected from $C_{1-6}$-alkyl, phenyl or pyridyl.

In another preferred embodiment of the invention $R^7$, $R^8$, $R^9$ are independently hydrogen; halogen; $C_{1-12}$-alkyl; $C_{3-6}$-cycloalkyl; cyano; cyanomethyl; perhalomethyl; sulfamoyl; $C_{1-6}$-alkylthio; $C_{1-6}$-alkylsulfonyl; $C_{1-6}$-alkylsulfinyl; arylthio, arylsulfinyl, arylsulfonyl, the aryl group optionally being mono-or polysubstituted with $C_{1-6}$-alkyl, halogen, hydroxy or $C_{1-6}$-alkoxy; $C_{1-6}$-alkoxycarbonyl-$C_{1-6}$-alkyl; carbamylmethyl; carboxy-$C_{1-6}$-alkyl; aryloxy; (1,2,4-oxadiazol-5-yl)- or (1,2,4-oxadiazol-3-yl)$C_{1-6}$-alkyl, the oxadiazolyl group optionally being substituted with $C_{1-6}$-alkyl or $C_{3-6}$-cycloalkyl; acyl; or a 5-6 membered nitrogen containing ring, optionally substituted with phenyl or $C_{1-6}$-alkyl.

Preferred compounds of the invention are:

3-Hydrazino-4H-pyrido[4,3-e]-1,2,4-thiadiazine 1,1-dioxide;

3-Benzylamino-4H-pyrido[4,3-e]-1,2,4-thiadiazine 1,1-dioxide;

3-(R)-(1-Phenylethylamino)-4H-pyrido[4,3-e]-1,2,4-thiadiazine 1,1-dioxide;

3-(S)-(1-Phenylethylamino)-4H-pyrido[4,3-e]-1,2,4-thiadiazine 1,1-dioxide;

3-Benzylamino-7-chloro-4H-pyrido[2,3-e]-1,2,4-thiadiazine 1,1-dioxide;

7-Chloro-3-(R)-(1-phenylethylamino)-4H-pyrido[2,3-e]-1,2,4-thiadiazine 1,1-dioxide;

7-Chloro-3-(S)-(1'-phenylethylamino)-4H-pyrido[2,3-e]-1,2,4-thiadiazine 1,1-dioxide;

3-Benzylamino-4H-pyrido[2,3-e]-1,2,4-thiadiazine 1,1-dioxide;

3-(R)-(1-Phenylethylamino)-4H-pyrido[2,3-e]-1,2,4-thiadiazine 1,1-dioxide;

3-(S)-(1-Phenylethylamino)-4H-pyrido[2,3-e]-1,2,4-thiadiazine 1,1-dioxide;

3-Hexylamino-4H-pyrido[4,3-e]-1,2,4-thiadiazine 1,1-dioxide;

7-Chloro-3-hexylamino-4H-pyrido[2,3-e]-1,2,4-thiadiazine 1,1-dioxide;

3-Octylamino-4H-pyrido[4,3-e]-1,2,4-thiadiazine 1,1-dioxide;

7-Chloro-3-octylamino-4H- pyrido[2,3-e]-1,2,4-thiadiazine 1,1-dioxide;

3-Allylamino-4H-pyrido[4,3-e]-1,2,4-thiadiazine 1,1-dioxide;

3-Allylamino-7-chloro-4H- pyrido[2,3-e]-1,2,4-thiadiazine 1,1-dioxide;

7-Chloro-3-(2-methoxy-1-methylethyl)amino-4H-pyrido[2,3-e]-1,2,4-thiadiazine 1,1-dioxide;

3-(2-Methoxy-1-methylethyl)amino-4H-pyrido[4,3-e]-1,2,4-thiadiazine 1,1-dioxide;

3-(2-Hydroxy-1-methylethyl)amino-4H-pyrido[4,3-e]-1,2,4-thiadiazine 1,1-dioxide;

3-Benzylamino-2-methyl-2H-pyrido[4,3-e]-1,2,4-thiadiazine 1,1-dioxide;

2-Isopropylamino-3,3-dimethoxy-3H-pyrido[2,3-b][1,4]thiazine 4,4-dioxide.

3-Methoxyamino-4H-pyrido[4,3-e]-1,2,4-thiadiazine 1,1-dioxide;

3-Ethoxyamino-4H-pyrido[4,3-e]-1,2,4-thiadiazine 1-1-dioxide;

3-Cyclopropylmethoxyamino-4H-pyrido[4,3-e]-1,2,4-thiadiazine 1,1-dioxide;

3-isopropoxyamino-4H-pyrido[4,3-e]-1,2,4-thiadiazine 1,1-dioxide;

3-Isobutoxyamino-4H-pyrido[4,3-e]-1,2,4-thiadiazine 1,1-dioxide;

3-Butoxyamino-4H-pyrido[4,3-e]-1,2,4-thiadiazine 1,1-dioxide;

3-Cyclopentyloxyamino-4H-pyrido[4,3-e]-1,2,4-thiadiazine 1,1-dioxide;

3-Allyloxyamino-4H-pyrido[4,3-e]-1,2,4-thiadiazine 1,1-dioxide;

3-Benzyloxyamino-4H-pyrido[4,3-e]-1,2,4-thiadiazine 1,1-dioxide;

3-(2-Phenylethoxy)amino-4H-pyrido[4,3-e]-1,2,4-thiadiazine 1,1-dioxide;

3-(2-Methylhydrazino)-4H-pyrido[4,3-e]-1,2,4-thiadiazine 1,1-dioxide;

3-(2-Ethylhydrazino)-4H-pyrido[4,3-e]-1,2,4-thiadiazine 1,1-dioxide;

3-(2-Isopropyihydrazino)-4H-pyrido[4,3-e]-1,2,4-thiadiazine 1,1-dioxide;

3-(2-Methyl-2-ethylhydrazino)-4H-pyrido[4,3-e]-1,2,4-thiadiazine 1,1-dioxide;

3-(2-Methyl-2-isopropylhydrazino)-4H-pyrido[4,3-e]-1,2,4-thiadiazine 1,1-dioxide;

3-(2,2,2-Trifluoroethyl)amino-4H-pyrido[4,3-e]-1,2,4-thiadiazine 1,1-dioxide;

3-(1,1,1,3,3,3-Hexafluoro-2-propyl)amino-4H-pyrido[4,3-e]-1,2,4-thiadiazine 1,1-dioxide;

3-(2-(1,1-Bis(trifluoromethyl)propyl))amino-4H-pyrido[4,3-e]-1,2,4-thiadiazine 1,1-dioxide 3-(1-Methyl-2,2,-difluoropropyl)amino-4H-pyrido[4,3-e]-1,2,4-thiadiazine 1,1-dioxide;

3-(1-Methyl-2,2-dicyanoethyl)amino-4H-pyrido[4,3-e]-1,2,4-thiadiazine 1,1-dioxide;

3-(2-Bicyclo[2,2,2]octyl)amino-4H-pyrido[4,3-e]-1,2,4-thiadiazine 1,1-dioxide;

3-(2-Adamantylamino)-4H-pyrido[4,3-e]-1,2,4-thiadiazine 1,1-dioxide;

3-(1-Adamantylamino)-4H-pyrido[4,3-e]-1,2,4-thiadiazine 1,1-dioxide;

3-(3-Quinuclidinyl)amino-4H-pyrido[4,3-e]-1,2,4-thiadiazine 1,1-dioxide;

3-(1,5-dimethylhexyl)amino-4H-pyrido[4,3-e]-1,2,4-thiadiazine 1,1-dioxide;

3-(3-methylhexyl)amino-4H-pyrido[4,3-e]-1,2,4-thiadiazine 1,1-dioxide;

3-(3-methylbutyl)amino-4H-pyrido[4,3-e]-1,2,4-thiadiazine 1,1-dioxide.

The compounds of the present invention interact with the potassium channels and hence act as openers or blockers of the ATP-regulated potassium channels, which make them useful in the treatment of various diseases of the cardiovascular system, e.g. cerebral ischemia, hypertension, ischemic heart diseases, angina pectoris and coronary heart diseases; the pulmonary system; the gastrointestinal system; the central nervous system and the endocrinological system.

Since some $K_{ATP}$-openers are able to antagonize vasospasms in basilar or cerebral arteries the compounds of the present invention can be used for the treatment of vasospastic disorders such as subarachnoid haemorrhage and migraine.

Potassium channel openers hyperpolarizes neurons and inhibit neurotransmitter release and it is expected that the present compounds can be used for the treatment of various diseases of the central nervous system, e.g. epilepsia, ischemia and neurodegenerative diseases, and for the management of pain.

By acting on potassium channels of the central nervous system the compounds of the present invention can be used for treatment of various neurological and psychiatric diseases such as Alzheimer, epilepsia and cerebral ischemia.

The compounds of the present invention may also be used for the treatment of diseases associated with decreased skelettal muscle blood flow such as Reynauds disease and intermittent claudication.

Further, the compounds of the invention may be used for the treatment of chronic airway diseases, including asthma, and for treatment of detrusor muscle instability secondary to bladder outflow obstruction and therefore for kidney stones by aiding their passage along the ureter. Potassium channel openers also relax urinary bladder smooth muscle, thus, the compounds of the present invention can be used for the treatment of urinary incontinence.

The present compounds could also be used for treatment of conditions associated with disturbances in gastrointestinal mobility such as irritable bowel syndrome. Additionally these compounds can be used for the treatment of premature labor and dysmenorrhea.

Further, potassium channel openers promote hairgrowth, therefore, the compounds of the present invention can be used for the treatment of baldness.

In diseases such as nesidioblastosis and insulinoma in which a hypersecretion of insulin causes severe hypoglycemia the compounds of the present invention can be used to reduce insulin secretion. In obesity hyperinsulinemia and insulin resistance is very frequently encountered. This condition could lead to the development of noninsulin dependent diabetes (NIDDM). It is expected that potassium channel openers and hence the compounds of the present invention can be used for contracting the hyperinsulinemia and thereby prevent diabetes and reduce obesity. In overt NIDDM treatment of hyperinsulinemia with potassium channel openers, and hence the present compounds, can be of benefit in restoring glucose sensitivity and normal insulin secretions.

In early cases of insulin dependent diabetes (IDDM) or in prediabetic cases, potassium channel openers and hence the present compounds can be used to induce betacell rest which may prevent the progression of the autoimmune disease.

Compounds of the present invention which act as blockers of $K_{ATP}$-channels can be used for the treatment of NIDDM.

Preferably, the compounds of the present invention may be used for treatment or prevention of diseases of the endocrinological system such as hyperinsulinemia and diabetes.

Accordingly, in another aspect the invention relates to a compound of the general formula I or a pharmaceutically acceptable acid addition salt thereof for use as a therapeutically acceptable substance, preferably for use as a therapeutically acceptable substance in the treatment of hyperinsulinemia and treatment or prevention of diabetes.

Furthermore, the invention also relates to the use of the inventive compounds of formula I as medicaments useful for treating hyperinsulinemia and treating or preventing diabetes.

In yet another aspect, the present invention relates to methods of preparing the above mentioned compounds. The methods comprises:

a) reacting a compound of formula II:

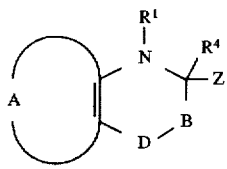

wherein A, B, D, $R^1$ and $R^4$ are as defined above and Z is a leaving group such as imidazol-1-yl, alkoxy, alkylthio, halogen, preferentially chloro, bromo, iodo, trimethylamino, or methylsulfonyl with a compound of formula III:

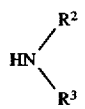

wherein $R^2$ and $R^3$ are defined above to form a compound of the general formula I using procedures described by e.g. T. H. Cronon et al., *J. Med. Chem.* 11, 136 (1968); L. Raffa et al., *Farmaco Ed. Sci.* 29, 411 (1974); B. Pirotte et al., *J. Med. Chem.* 36, 3211 (1993).

Another method comprises:

b) reacting a compound of formula IV:

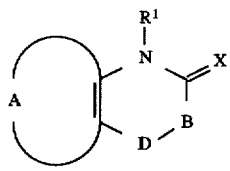

wherein $R^1$ is hydrogen and A, B, D and X are as defined above, or B is NH and $R^1$, A, D and X are as defined above, with the compound of formula II, or a suitable salt thereof in the presence of $P_2O_5$ and a high boiling tertiary amine or a suitable salt thereof using a procedure described by Jensen K. G. and Pedersen E. B., *Chem. Scr.*, 20, 248–250 (1988) and Andersen L., Nielsen F. E. and Pedersen E. B., *Chem. Scr.*, 29, 45–49 (1989), to form a compound of the general formula I.

c) reacting a compound of the formula IV:

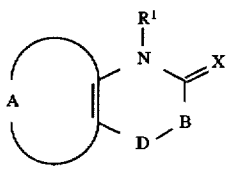

wherein $R^1$ is hydrogen and A, B, D and X are as defined above or B is NH and $R^1$, A, D and X are as defined above, with a compound of the formula III, or a suitable salt thereof in the presence of titanium tetrachloride and a solvent with which it may form a complex, like e.g. tetrahydrofuran, or a mixture of toluene and anisole, according to the methods described in R. I. Fryer, J. V. Earley, G. F. Field, W. Zally, and L. H. Sternbach, *J.Org.Chem.* 34,1143–1145 (1969); J. B. Press et al., *J.Med.Chem.* 22 725–731 (1979); or G. Roma et al. *Eur.J.Med.Chem.* 26, 489–496 (1991), to form a compound of the general formula I.

d) reacting a compound of formula V

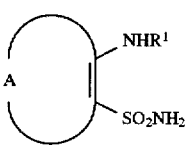

wherein $R^1$ and A are as defined above, with a compound of formula VI

wherein $R^3$ is as defined above using the method described by Chern J. W. et al., *J. Heterocycl. Chem.*, 27, 1909–1915 (1990), to form a compound of the general formula I wherein D is $SO_2$, B is $>NR^5$, $R^2$ is H, and $R^4$ and $R^5$ together form a bond.

e) reacting a compound of the formula V

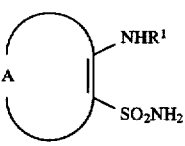

wherein $R^1$ and A are as defined above, with a compound of formula VII $R^3NHC(=O)Cl$ (VII)

wherein $R^3$ is as defined above using the method described by Chem J. W. et al., *J. Heterocycl Chem.*, 27, 1909–1915 (1990), to form a compound of the general formula I, wherein D is $SO_2$, B is $>NR^5$, $R^2$ is H, and $R^4$ and $R^5$ together form a bond.

f) reacting a compound of the formula V

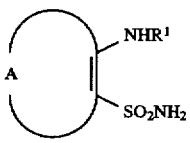

wherein $R^1$ and A are defined as above, with a compound of formula VIII

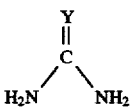

wherein Y is NH or S, or a suitable salt thereof using procedures described by Kotovskaya S. K. et al., *Khim.-Farm. Zh.*, 13, 54–57 (russ.) (1979) and Topliss J. G. et al., *J. Org. Chem.*, 28, 2313 (1963), to form a compound of the general formula I, wherein D is $SO_2$, B is $>NR^5$, $R^4$ and $R^5$ together form a bond, and $R^2$ and $R^3$ are H.

The starting materials are either known compounds or compounds which may be prepared in analogy with the preparation of known compounds or in analogy with known methods as described by e.g Huang B.-S., et al., J. Med. Chem., 23, 575-7 (1980), Ofitserov V. 1. et al., *Khim. Geterotsikl. Soedin.*, 1119–22 (russ.) (1976), Topliss J. G., U.S. Pat. No. 3,641,017 (1972), Kotovskaya S. K. et al., *Khim.-Farm. Zh.*, 13, 54–57 (russ.) (1979), Meyer R. F., *J. Heterocycl. Chem.*, 6, 407–408 (1969) and Hattori M., Yoneda M., and Goto M., *Bull. Chem. Soc. Jap.*, 46, 1890–1 (1973), Williams T. R. and Cram D. J., *J. Org. Chem.*, 38, 20–26 (1973), Barnes A. C., Kennewell P. D. and Taylor J.

B., *J. Chem. Soc. Chem. Commun.*, 1973, 776–777, Stoss and Satzinger, *Chem. Ber.*, 109, 2097 (1976), Kresze G., Hatjiissaak A., *Phosphorus Sulfur*, 29, 41–47 (1987), Dillard R. D., Yen T. T., Stark P., Pavey D. E., *J. Med. Chem.*, 23, 717–722 (1980).

PHARMACOLOGICAL METHODS

The ability of the compounds to interact with potassium channels can be determined by various methods. When patch-clamp techniques (Hamill O. P., Marty A., Nefer E., Sakman B. and Sigworth F. J., *Plugers Arch.*, 391, 85–100 (1981)) are used the ionic current through a single channel of a cell can be recorded.

The activity of the compounds as potassium channel openers can also be measured as relaxation of rat aortas rings according to the following procedure:

A section of rat thoracic aorta between the aortic arch and the diaphragm was dissected out and mounted as ring preparations as described by Taylor P. D. et al , *Brit J. Pharmacol*, 111, 42–48 (1994).

After a 45 min. equilibration period under a tension of 2 g, the preparations were contracted to achieve 80% of the maximum response using the required concentration of phenylephrine. When the phenylephrine response reached a plateau, potential vasodilatory agents were added cumulatively to the bath in small volumes using half log molar increments at 2 min intervals. Relaxation was expressed as the percentage of the contracted tension. The potency of a compound was expressed as the concentration required to evoke a 50% relaxation of the tissue.

In the pancreatic β-cell the opening of the $K_{ATP}$-channels can be determined by measuring the subsequent change in the concentration of cytoplasmic free $Ca^{2+}$ concentration according to the method of Arkhammer P. et al., *J. Biol. Chem.*, 262, 5448–5454 (1987).

$^{86}Rb^+$ efflux from a β-cell line

The RIN 5F cell line was grown in RPMI 1640 with Glutamax I, supplemented with 10% fetal calf serum (from GibcoBRL, Scotland, UK) and maintained in an atmosphere of 5% $CO_2$/ 95% air at 37° C. The cells were detached with a Trypsin-EDTA solution (from GibcoBRL, Scotland, UK), resuspended in medium, added 1 mCi/ml $^{86}Rb^+$ and replated into microtiter plates (96 well cluster 3596, sterile, from Costar Corporation, MA, USA) at a density of 50000 cells/well in 100 ml/well, and grown 24 hours before use in assay.

The plates were washed 4 times with Ringer buffer (150 mM NaCl, 10 mM Hepes, 3.0 mM KCl, 1.0 mM $CaCl_2$, 20 mM Sucrose, pH 7.1). Eighty ml Ringer buffer and 1 μl control- or test compound dissolved in DMSO was added. After incubation 1 h at room temperature with a lid, 50 μl of the supernatant was transferred to PicoPlates (Packard Instrument Company, CT, USA) and 100 μl MicroScint40 (Packard Instrument Company, CT, USA) added. The plates were counted in TopCount (Packard Instrument Company, CT, USA) for 1 min/well at the $^{32}P$ program.

The calculation of $EC_{50}$ and $E_{max}$ was done by SlideWrite (Advanced Graphics Software, Inc., CA, USA) using a four parameter logistic curve: $y=(a-d)/(1+(x/c)^b)+d$, where a=the activity estimated at concentration zero, b=a slope factor, c=the concentration at the middle of the curve and, d=the activity estimated at infinite concentration. $EC_{50}=c$ and $E_{max}=d$, when the curve is turned of at infinite concentrations.

Measurement of Insulin Release from Incubated Pancreatic Islets Isolated by the Collagenase Method from Fed Female Albino Wistar Rats.

Groups of 10 islets, each derived from the same batch of islets, are preincubated for 30 min at 37° C. in 1 ml of a bicarbonate buffered solution (in mM: NaCl 115, KCl 5, $CaCl_2$ 2.56, $MgCl_2$ 1, $NaHCO_3$ 24) supplemented with 2.8 mM glucose, 0.5% (w/v) dialysed albumin (fraction V, Sigma Chemical Co and equilibrated against a mixture of $O_2$ (95%) and $CO_2$ (5%). The groups of 10 islets are then incubated at 37° C. for a further 90 min in 1 ml of the same bicarbonate buffered medium containing 16.7 mM glucose and, in addition, the selected test compounds.

In this procedure 6 to 8 series of 10 beakers are incubated simultaneously. For each serie, 8 beakers contain groups of 10 islets and 2 beakers are considered as control beakers (treated in the same manner, containing physiological medium but no islets). In order to ensure homogeneous distribution of islets among the different series, the collected islets are placed in succession in one beaker of each serie. The first and last series of 10 beakers (8 beakers with islets, 2 beakers without islets in each series) are incubated in the presence of 16.7 mM glucose (no added pharmacological compound; these series are regarded as control series). The 4–6 other series of 10 beakers are incubated in a 16.7 mM glucose medium enriched with the selected pharmacological compound (either different compounds or 1 or 2 compounds tested at different concentrations). After incubation, the incubation medium is removed from the beaker with a Pasteur pipette and stored at −20° C. The release of insulin is measured radioimmunologically using rat insulin as a standard. Experiments are repeated 2–4 times, on different days (which means on 2–4 different sources of pancreatic islets).

The islets-related variations (variations in the absolute values for insulin secretion from one to another immunoassay) led us to express the secretory rate with reference to a control value (100%=average of absolute values of the first and last series of beakers in each experiment: control series). Thus for each experimental series, the absolute values are expressed as % compared to the control condition within the same experiment.

At a concentration of 50 μM several compounds potently inhibit insulin release:

| Compound No. | % Residual insulin released |
|---|---|
| 1 | 75 |
| 3 | 17.5 |
| 6 | 52.3 |

The compounds according to the invention are effective over a wide dosage range. In general satisfactory results are obtained with dosages from about 0.05 to about 1000 mg, preferably from about 0.1 to about 500 mg, per day. A most preferable dosage is about 5 mg to about 200 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet, appropriate for use in this method, may be prepared by conventional tabletting techniques and contains:

| Active compound | 5.0 mg |
| Lactosum | 67.8 mg Ph.Eur. |
| Avicel ® | 31.4 mg |
| Amberlite ® | 1.0 mg |
| Magnesii stearas | 0.25 mg Ph.Eur. |

Due to their high degree of activity, the compounds of the invention may be administered to an animal in need of such treatment, prevention, elimination, alleviation or amelioration of various diseases as mentioned above and especially of diseases of the endocrinological system such as hyperinsulinemia and diabetes. Such animals include both domestic animals, e.g. household pets, and non-domestic animals such as wildlife. Preferably the animal is a mammal especially a human.

EXAMPLES

The process for preparing compounds of formula I and preparations containing them is further illustrated in the following examples which, however, are not to be construed as limiting.

EXAMPLE 1
Preparation of intermediates
3-Methylsulfanyl-4H-pyrido[4,3-e]-1,2,4-thiadiazine 1,1-dioxide monohydrate (Compound I), was prepared according to the published procedure (B. Pirotte et al., J.Med.Chem.,1993, 36, 3211–3213.

7-Chloro-3-(imidazol-1-yl)-4H-pyrido[2,3-e]-1,2,4-thiadiazine 1,1-dioxide

A solution of 2-amino-5-chloropyridine-3-sulfonamide (8.0 g) and thiocarbonyldiimidazole (20.5 g) in dioxane (80 mL) and DMF (20 mL) was refluxed for 3 h. The reaction was checked by t.l.c. When the reaction was complete, the solvents were removed under reduced pressure. The residue was dissolved in an aqueous solution of NaOH (4 g in 150 mL of water). The solution turns rapidly to a suspension of the sodium salt of the title compound. The salt was collected by filtration and washed with a small volume of water. The salt was dissolved in hot water (200 mL), treated with charcoal, filtered and the filtrate was adjusted to pH 5–6 with 1N HCl. The precipitate was collected by filtration, washed with water and dried (yield: 8.8 g); m.p. 330°–331° C. (Compound II).

3-(Imidazol-1-yl-4H-pyrido[2,3-e]-1,2,4-thiadiazine 1,1-dioxide

The same procedure as described for Compound II was used starting from 2-aminopyridine-3-sulfonamide (5.0 g) and thiocarbonyldiimidazole (13 g) except that the sodium salt did not precipitate after the addition of NaOH. The alcaline solution was treated with charcoal, filtered and the filtrate was adjusted to pH 5–6 with HCl 1N. The precipitate was collected by filtration, washed with water and dried (yield: 4.8 g); m.p. 312°–314° C. (Compound III).

2-Methyl-3-thioxo-2,3-dihydro-4H-pyrido[4,3-e]-1,2,4-thiadiazine 1,1-dioxide

A solution of N-methyl-4-aminopyridine-3-sulfonamide (de Tullio et al., Tetrahedron 1995, 3221–3234) (5.0 g) and thiocarbonyldiimidazole (7.5 g) in dioxane (30 mL) and DMF (15 mL) was heated at 90° C. for 2 h. The solvents were removed by distillation under reduced pressure. The residue was dispersed in 0.6N NaOH (20 mL) and stirred for 30 min. The alkaline solution was treated with charcoal, filtered, and the filtrate was adjusted to pH 4–5. The precipitate was collected by filtration, washed with water and dried (yield: 4 g); m.p. 195°–198° C. (Compound IV).

2-Methyl-3-methylsulfanyl-2H-pyrido[4,3-e]-1,2,4-thiadiazine 1,1-dioxide

A solution of 2-methyl-3-thioxo-2,3-dihydro-4H-pyrido [4,3-e]-1,2,4-thiadiazine 1,1-dioxide (1.0 g) in acetonitrile (20 mL) was supplemented with potassium carbonate (1.0 g), then with methyl iodide (1 mL). After 1 h at room temperature, the solvent was removed by distillation under reduced pressure. The residue was dispersed in water (50 mL) and the suspension was adjusted to pH 5 with formic acid. The insoluble material was collected by filtration, washed with water and dried (yield: 0.8 g); m.p. 135°–138° C. (Compound V).

1H-Pyrido[2,3-b][1,4]thiazin-2(3H)-thione

Thionation of 1H-pyrido[2,3-b][1,4]thiazin-2(3H)-one (prepared according to Dunn and Norrie, J.Prakt.Chem. 1990,332 (4) 444–452) with phosphorous pentasulfide in toluene by standard procedures (see e.g. H. Tawada et al., Chem.Pharm.Bull. 1990, 38, 1238–1245) gave the title compound; m.p. 233°–234° C. (Compound VI).

2-Isopropylamino-3H-Pyrido[2,3-b][1,4]thiazine

1H-Pyrido[2,3-b][1,4]thiazin-2(3H)-thione (0.5 g) was dissolved in 10 ml of isopropylamine and allowed to stand for 45 min at room temperature. Then the excess of the amine was removed in vacuum and the solid residue was dissolved in 25 ml of ethyl acetate I methanol (4:1), treated with charcoal and filtered through a pad of silica. The filter was eluted with 2×10 ml of ethyl acetate/methanol (4:1). The filtrate was evaporated and the slowly crystallizing residue was triturated with 5 ml of ethyl acetate and then with 3 ml of diethyl ether. The crystals were filtered off and dried to give the title compound; m.p. 135°–139° C. (Compound VII).

EXAMPLE 2
3-Hydrazino-4H-pyrido|4,3-e|-1,2,4-thiadiazine 1,1-dioxide

3-Methylsulfanyl-4H-pyrido|4,3-e|-1,2,4-thiadiazine 1,1-dioxide monohydrate (1.0 g) was added to hydrazine hydrate (0.8 ml) and the mixture was heated to 70° C. for 30 min. After cooling, the reaction mixture was supplemented with methanol (10 ml) and the solvents were removed by distillation under reduced pressure. The residue was dissolved in NaOH 2M (20 ml), treated with charcoal, filtered, and the filtrate was adjusted to pH 6–7 with HCl 1M. The precipitate so obtained was collected by filtration, washed with water an dried (yield: 0.8 g); m.p. 290°–292° C. (Compound 1).

EXAMPLE 3
3-Aralkylamino-4H-1,2,4-pyridothiadiazine 1,1-dioxides

A mixture of the appropriate precursor (Compound I, II, or III) (0.5 g) and the appropriate aralkylamine (2.5 mL) was refluxed for 30 min to 60 min (until completion of the reaction ; t.l.c.). After cooling, the reaction mixture was distributed between 0.5% aqueous NaOH (200 mL) and diethylether (100 mL). The aqueous layer was separated and was treated with charcoal, then filtered. The filtrate was adjusted to pH 6–7 with formic acid. The resulting precipitate was collected by filtration, washed with water and dried (yield: 70–85%).

In this way the following compounds were prepared:

3-Benzylamino-4H-pyrido[4,3-e]-1,2,4-thiadiazine 1,1-dioxide; m.p. 198°–201° C. (Compound 2

3-(R)-(1-Phenylethylamino)-4H-pyrido|4,3-e|-1,2,4-thiadiazine 1,1-dioxide; m.p. 236°–238° C. (Compound 3).

3-(S)-(1-Phenylethylamino)-4H-pyrido|4,3-e|-1,2,4-thiadiazine 1,1-dioxide; m.p. 233°–235° C. (Compound 4).

3-Benzylamino-7-chloro-4H-pyrido[2,3-e]-1,2,4-thiadiazine 1,1-dioxide; m.p. 244°–245° C. (Compound 5).

7—Chloro-3-(R)-(1-phenylethylamino)-4H-pyrido[2,3-e|-1,2,4-thiadiazine 1,1-dioxide; m.p. 261°–262° C. (Compound 6).

7-Chloro-3-(S)-(1-phenylethylamino)-4H-pyrido[2,3-e]-1,2,4-thiadiazine 1,1-dioxide; m.p. 262°–265° C. (Compound 7).

3-Benzylamino-4H-pyrido[2,3-e]-1,2,4-thiadiazine 1,1-dioxide; m.p. 232°–233° C. (Compound 8

3-(R)-(1-Phenylethylamino)-4H-pyrido[2,3-e]-1,2,4-thiadiazine 1,1-dioxide; m.p. 207°–210° C. (Compound 9).

3-(S)-(1-Phenylethylamino)-4H-pyrido[2,3-e]-1,2,4-thiadiazine 1,1-dioxide; m.p. 213°–214° C. (Compound 10).

EXAMPLE 4
3-Hexylamino-4H- pyrido|4,3-e|-1,2,4-thiadiazine 1,1-dioxide

3-Methylsulfanyl-4H-pyrido[4,3-e]-1,2,4-thiadiazine 1,1-dioxide monohydrate (0.5 g) and hexylamine (5.0 mL) were refluxed for 3–4 h (until completion of the reaction ; t.l.c.). The amine was distilled under reduced pressure. The residue was dissolved in 1N NaOH (150 mL), treated with charcoal, filtered, and the filtrate was adjusted to pH 5–6 with formic acid. The resulting precipitate was collected by filtration, washed with water and dried (yield: 0.38 g); m.p. 170°–171° C. (Compound In a similar manner the following compound was prepared: 7—Chloro-3-hexylamino-4H- pyrido|2,3-e|-1,2,4-thiadiazine 1,1-dioxide; m.p. 176–179° C.; from 7-chloro-3-(imidazol-1-yl)-4H-pyrido[2,3-e]-1,2,4-thiadiazine 1,1-dioxide and hexylamine.(Compound 12).

EXAMPLE 5
3-Octylamino-4H-pyrido|4,3-e|-1,2,4-thiadiazine 1,1-dioxide

A mixture of 3-methylsulfanyl-4H-pyrido|4,3-e|-1,2,4-thiadiazine 1,1-dioxide monohydrate (0.5 g), octylamine (0.5 mL) and m-chlorotoluene (3 mL) was refluxed for 2–3 h (until completion of the reaction; t.l.c.). Most of the solvents were removed by distillation and the residue was dispersed in a mixture of water (30 mL) and methanol (30 mL) and supplemented with NaOH 10% w/v in water (2 mL). The mixture was treated with charcoal, filtered, and the filtrate was adjusted to pH 6 with 1N HCl. The resulting precipitate was collected by filtration, washed with water and dried (yield: 0.29 g); m.p. 176°–179° C. (Compound 13).

In a similar manner the following compound was prepared:

7-Chloro-3-octylamino-4H- pyrido[2,3-e]-1,2,4-thiadiazine 1,1-dioxide; m.p. 170°–175° C.; from 7-chloro-3-(imidazol-1-yl)-4H-pyrido[2,3-e]-1,2,4-thiadiazine 1,1-dioxide and octylamine. (Compound 14).

EXAMPLE 6
3-Allylamino-4H-pyrido[4,3-e]-1,2,4-thiadiazine 1,1-dioxide

A mixture of 3-methylsulfanyl-4H-pyrido[4,3-e]-1,2,4-thiadiazine 1,1-dioxide monohydrate (0.5 g) and allylamine (4 mL) was heated in a sealed bumb for 4–5 h at 120° C. After cooling, the amine was removed by distillation under reduced pressure. The residue was dissolved in 0.5N NaOH, treated with charcoal, filtered, and the filtrate was adjusted to pH 6 with 1N HCl. The resulting precipitate was collected by filtration, washed with water and dried to give the title compound as a dihydrate (yield: 0.44 g); m.p. 206°–208° C. (Compound 15).

In a similar manner the following compound was prepared:

3-Allylamino-7-chloro-4H-pyrido[2,3-e]-1,2,4-thiadiazine 1,1-dioxide; m.p. 224°–227° C. from 7-chloro-3-(imidazol-1-yl)-4H-pyrido[2,3-e]-1,2,4-thiadiazine 1,1-dioxide and allylamine. (Compound 16).

EXAMPLE 7
7-Chloro-3-(2-methoxy-1-methylethyl)amino-4H-pyrido|2,3-e]-1,2,4-thiadiazine 1,1-dioxide A mixture of 7-chloro-3-(imidazol-1-yl)-4H-pyrido|2,3-e|-1,2,4-thiadiazine (0.5 g) and 2-amino-1-methoxypropane (5 mL) was refluxed for 24 h. The amine was removed by distillation under reduced pressure. The residue was dissolved in a small volume of 0.1N NaOH (20 mL), treated with charcoal, filtered and the filtrate was adjusted to pH 5–6. The suspension was conserved 24 h at +4° C. The precipitate was collected by filtration, washed with the minimum of water and dried (yield: 0.25 g); m.p. 150°–156° C. (Compound 17).

EXAMPLE 8

3-(2-Methoxy-1-methylethyl)amino-4H-pyrido[4,3-e]-1,2,4-thiadiazine 1,1-dioxide

The same procedure than above was used (except the starting material was 3-methylsulfanyl-4H-pyrido[4,3-e]-1,2,4-thiadiazine 1,1-dioxide monohydrate) up to the adjustment of the aqueous solution to pH 5–6. However, in this case, no precipitation occured. Then, the solvent was removed by distillation under reduced pressure. The residue was dispersed in a small volume of water (4 mL). The insoluble material was collected by filtration. The solid was dispersed in acetone (30 mL). The insoluble material was eliminated by filtration. The filtrate was concentrated under reduced pressure. The residue was solubilized in a small volume of acetone (3 mL). After a few minutes, a fine precipitate appears which was collected by filtration, washed with acetone and dried to give the title compound as a monohydrate (yield: 0.1 g); m.p. 174°–178° C. (Compound 18).

EXAMPLE 9

3-(2-Hydroxy-1-methylethyl)amino-4H-pyrido[4,3-e]-1,2,4-thiadiazine 1,1-dioxide

A suspension of 3-methylsulfanyl-4H-pyrido[4,3-e]-1,2,4-thiadiazine 1,1-dioxide monohydrate and 2-amino-1-propanol (0.75 mL) was refluxed for 90 min (until completion of the reaction; t.l.c.). After cooling, the addition of diethylether (20 mL) gave rise to the separation of an oily residue. After decantation of the etheral solution, the residue was solubilized in methanol (1 mL) and then supplemented with diethylether (15 mL). An oily residue separated again. After decantation of the supernatent, the oily residue was solubilized in acetone (6 mL). A fine precipitate readily appeared. After 3 h at +4° C., the resulting precipitate was collected by filtration, washed with acetone and dried (yield: 0.33 g); m.p. 213°–216° C. (Compound 19).

EXAMPLE 10

3-Benzylamino-2-methyl-2H-pyrido[4,3-e]-1,2,4-thiadiazine 1,1-dioxide

A solution of 2-methyl-3-methylsulfanyl-2H-pyrido[4,3-e]-1,2,4-thiadiazine 1,1-dioxide (0.5 g) and benzylamine (0.5 mL) in dioxane (2.5 mL) was refluxed until completion of the reaction (t.l.c.). After cooling, the addition of ether gave rise to the precipitation of the title compound. The precipitate was collected by filtration, washed with ether and recrystallized from methanol-ether (yield: 0.4 g); m.p. 142°–146° C. (Compound 20).

EXAMPLE 11

2-Isoproiylamino-3,3-dimethoxy-3H-pyrido[2,3-b][1,4]thiazine 4,4-dioxide

To a stirred solution of 2-isopropylamino-3H-pyrido[2,3-b][1,4]thiazine (0.10 g) in 2 ml of methanol was added 2 ml of water. To the resulting turbid mixture oxone (0.59 g) was added over 10 min and stirring was continued for 1 h. Then 10 ml of water was added and the mixture was extracted 3 times with 5 ml of dichloromethane. The combined extracts were dried over sodium sulfate and the solvent was removed in vacuum. The residue was purified on a silica column eluted with a 9:1 mixture of ethyl acetate and methanol to give the title compound; m.p. 123–126° C.; m/e 299 (M+); $^1$H-NMR(CDCl$_3$), δ (ppm): 7.92 (m, 1H, 6-H), 7.39–7.23 (m, 7-H and residual chloroform), 7.16–7.07 (m, 1H, 8-H), 5.79 (br d, 1H, NH), 4.2–4.0 (m, 1H, CH), 3.66 (s, 3H, CH$_3$O), 3.57 (s, 3H, CH$_3$O), 1.35–1.26 (two d, 6H, (CH$_3$)$_2$C). (Compound 21).

What is claimed is:

1. A compound of formula I

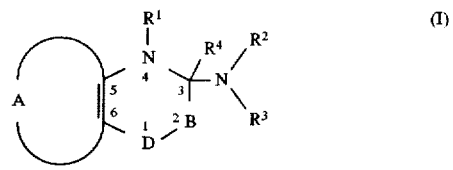

wherein

B is NR$^5$ wherein R$^5$ is (1) hydrogen, (2) hydroxy, (3) C$_{1-6}$-alkoxy, (4) C$_{1-6}$-alkyl, (5) C$_{3-6}$-cycloalkyl, (6) C$_{2-6}$-alkenyl, or (7) C$_{2-6}$-alkynyl, wherein (4) to (7) are optionally mono- or polysubstituted with halogen, or R$^1$ and R$^4$ together form a bond;

D is —S(=O)— or D—B is —S(=O)(R$^{10}$)=N— wherein R$^{10}$ is (1) C$_{1-6}$-alkyl, (2) aryl or (3) heteroaryl, wherein (2) and (3) are optionally mono- or polysubstituted with halogen, hydroxy, C$_{1-6}$-alkoxy, aryloxy, arylalkoxy, nitro, amino, C$_{1-6}$-monoalkyl- or dialkylamino, cyano, acyl, or C$_{1-6}$-alkoxycarbonyl;

R$^1$ is (1) hydrogen, (2) hydroxy, (3) C$_{1-6}$-alkoxy, (4) C$_{1-6}$-alkyl, (5) C$_{3-6}$-cycloalkyl, (6) C$_{2-6}$-alkenyl or (7) C$_{2-6}$-alkynyl, wherein (4) to (7) are optionally mono- or polysubstituted with halogen and R$^4$ is hydrogen, or R$^4$ together with R$^5$ form a bond, or R$^1$ together with R$^4$ form a bond;

R$^2$ is (1) hydrogen, (2) hydroxy, (3) C$_{1-6}$-alkoxy, (4) C$_{1-6}$-alkyl, (5) C$_{3-6}$-cycloalkyl, (6) C$_{2-6}$-alkenyl, or (7) C$_{2-6}$-alkynyl, wherein (4) to (7) are optionally mono- or polysubstituted with halogen;

R$^3$ is (1) R$^{11}$, (2) —OR$^{11}$, (3) —C(=X)R$^{11}$, (4) —NR$^{11}$R$^2$, (5) bicycloalkyl, (6) aryl, (7) heteroaryl, (8) arylalkyl or (9) heteroarylalkyl, wherein (5) to (9) are optionally mono- or polysubstituted with halogen, hydroxy, C$_{1-6}$-alkoxy, aryloxy, arylalkoxy, nitro, amino, C$_{1-6}$-monoalkyl- or dialkylamino, cyano, oxo, acyl or C$_{1-6}$-alkoxycarbonyl, or (10) aryl substituted with C$_{1-6}$-alkyl, wherein X is O or S;

R$^{11}$ is (1) hydrogen, (2) C$_{3-6}$-cycloalkyl, (3) (C$_{3-6}$-cycloalkyl)C$_{1-6}$-alkyl, wherein the C$_{3-6}$-cycloalkyl group in (2) and (3) is optionally mono- or polysubstituted with C$_{1-6}$-alkyl, halogen, hydroxy or C$_{1-6}$-alkoxy, (4) a 3-6 membered saturated ring system comprising one or more nitrogen-, oxygen- or sulfur atoms, or (5) straight or branched C$_{1-18}$-alkyl optionally mono- or polysubstituted with halogen, hydroxy, C$_{1-6}$-alkoxy, C$_{1-6}$-alkylthio, C$_{3-6}$-cycloalkyl, aryl, aryloxy, arylalkoxy, nitro, amino, C$_{1-6}$-monoalkyl- or dialkylamino, cyano, oxo, formyl, acyl, carboxy, C$_{1-6}$-alkoxycarbonyl, or carbamoyl;

R$^{12}$ is (1) hydrogen, (2) C$_{1-6}$-alkyl, (3) C$_{2-6}$-alkenyl, or (4) C$_{3-6}$-cycloalkyl optionally mono- or polysubstituted with C$_{1-6}$-alkyl, halogen, hydroxy or C$_{1-6}$-alkoxy, or R$^{11}$ and R$^{12}$ together with the nitrogen atom form a 3-12 membered mono- or bicyclic system, in which one or more of the carbon atoms may be exchanged with nitrogen, oxygen or sulfur, each of these ring systems optionally being mono- or polysubstituted with halogen, C$_{1-6}$-alkyl, hydroxy, C$_{1-6}$-alkoxy, C$_{1-6}$-alkoxy-C$_{1-6}$-alkyl, nitro, amino, cyano, trifluoromethyl, C$_{1-6}$-monoalkyl- or dialkylamino, or oxo, or

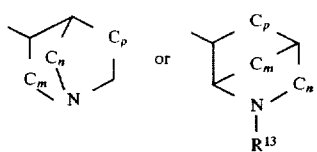

wherein n, m, p independently are 0, 1, 2, or 3 and R³ is (1) hydrogen, (2) hydroxy, (3) $C_{1-6}$-alkoxy, (4) $C_{3-6}$-cycloalkyl optionally mono- or polysubstituted with $C_{1-6}$-alkyl, halogen, hydroxy or $C_{1-6}$-alkoxy, (5) $C_{1-6}$-alkyl, (6) $C_{2-6}$-alkenyl, or (7) $C_{2-6}$-alkynyl, wherein (5) to (7) are optionally mono- or polysubstituted with halogen, or R² and R³ together with the nitrogen atom form a 3-12 membered mono- or bicyclic system, in which one or more of the carbon atoms may be exchanged with nitrogen, oxygen or sulfur, each of these ring systems optionally being mono- or polysubstituted with halogen, $C_{1-6}$-alkyl, hydroxy, $C_{1-6}$-alkoxy, $C_{1-6}$-alkoxy-$C_{1-6}$-alkyl, nitro, amino, cyano, trifluoromethyl, $C_{1-6}$-monoalkyl- or dialkylamino or oxo; and A together with carbon atoms 5 and 6 of formula I form a pyridine ring selected from

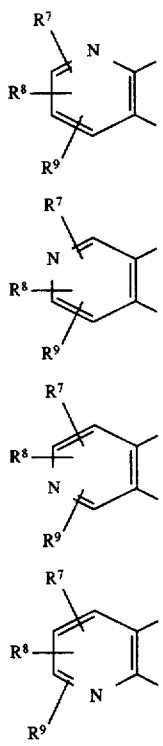

wherein R⁷, R⁸, R⁹ independently are (1) hydrogen, (2) halogen, (3) $C_{1-12}$-alkyl, (4) $C_{3-6}$-cycloalkyl, (5) hydroxy, (6) $C_{1-6}$-alkoxy, (7) $C_{1-6}$-alkoxy-$C_{1-6}$-alkyl, (8) nitro, (9) amino, (10) cyano, (11) cyanomethyl, (12) perhalomethyl, (13) $C_{1-6}$-monoalkyl- or dialkylamino (14) sulfamoyl, (15) $C_{1-6}$-alkylthio, (16) $C_{1-6}$-alkylsulfonyl, (17) $C_{1-6}$-alkylsulfinyl, (18) $C_{1-6}$-alkylcarbonylamino, (19) arylthio, (20) arylsulfinyl, (21) arylsulfonyl, wherein the aryl group in (19) to (21) is optionally mono- or polysubstituted with $C_{1-6}$-alkyl, halogen, hydroxy or $C_{1-6}$-alkoxy, (22) $C_{1-6}$-alkoxycarbonyl, (23) $C_{1-6}$-alkoxycarbonyl-$C_{1-6}$-alkyl, (24) carbamyl, (25) carbamylmethyl, (26) $C_{1-6}$-monoalkyl- or dialkylaminocarbonyl, (27) $C_{1-6}$-monoalkyl- or dialkylaminothiocarbonyl, (28) ureido, (29) $C_{1-6}$-monoalkyl- or dialkylaminocarbonylamino, (30) thioureido, (31) $C_{1-6}$-monoalkyl- or dialkylaminothiocarbonylamino, (32) $C_{1-6}$-monoalkyl- or dialkylaminosulfonyl, (33) carboxy, (34) carboxy-$C_{1-6}$-alkyl, (35) acyl, (36) aryl, (37) arylalkyl, (38) aryloxy, wherein the aryl group in (36) to (38) is optionally mono- or polysubstituted with $C_{1-6}$-alkyl, halogen, hydroxy or $C_{1-6}$-alkoxy, (39) (1,2,4-oxadiazol-5-yl)-$C_{1-6}$-alkyl, (40) (1,2,4-oxadiazol-3-yl)-$C_{1-6}$-alkyl, wherein the oxadiazolyl group in (39) and (40) is optionally substituted with $C_{1-6}$-alkyl or $C_{3-6}$-cycloalkyl, or (41) a 5-6 membered nitrogen containing ring, optionally substituted with phenyl or $C_{1-6}$-alkyl; or a pharmaceutical acceptable salt thereof with a pharmaceutically acceptable acid or base; an optical isomer thereof; or a tautomeric form thereof.

2. A compound of claim 1, wherein R² is hydrogen or $C_{1-6}$-alkyl.

3. A compound of claim 1, wherein R³ is (1) R¹¹, (2) —OR¹¹, (3) —NR¹¹R¹² or (4) aryl, the aryl groups optionally being substituted with $C_{1-6}$-alkyl, wherein R¹¹ is (1) hydrogen, (2) $C_{3-6}$-cycloalkyl, (3) ($C_{3-6}$-cycloalkyl)$C_{1-6}$-alkyl, (4) a 3-6 membered saturated ring system comprising one, two or three nitrogen—, oxygen— or sulfur atoms, or (5) straight or branched $C_{1-18}$-alkyl optionally substituted with halogen, hydroxy, $C_{1-6}$-alkoxy, $C_{1-6}$-alkylthio, $C_{3-6}$-cycloalkyl or aryl, R¹² is hydrogen, $C_{1-6}$-alkyl or $C_{3-6}$-cycloalkyl, or R¹¹ and R¹² together with the nitrogen atom form a 4-6 membered ring.

4. A compound of claim 1, wherein R³ is secondary $C_{3-6}$-alkyl, tertiary $C_{4-6}$-alkyl, $C_{3-6}$-cycloalkyl or ($C_{3-6}$-cycloalkyl)methyl.

5. A compound of claim 1, wherein R⁷, R⁸, R⁹ independently are (1) hydrogen, (2) halogen, (3) $C_{1-12}$-alkyl, (4) $C_{3-6}$-cycloalkyl, (5) cyano, (6) cyanomethyl, (7) perhalomethyl, (8) sulfamoyl, (9) $C_{1-6}$-alkylthio, (10) $C_{1-6}$-alkylsulfonyl, (11) $C_{1-6}$-alkylsulfinyl, (12) arylthio, (13) arylsulfinyl, (14) arylsulfonyl, wherein the aryl group in (12) to (14) is optionally mono- or polysubstituted with $C_{1-6}$-alkyl, halogen, hydroxy or $C_{1-6}$-alkoxy, (15) $C_{1-6}$-alkoxycarbonyl-$C_{1-6}$-alkyl, (16) carbamylmethyl, (17) carboxy-$C_{1-6}$-alkyl, (18) aryloxy, (19) (1,2,4-oxadiazol-5-yl)$C_{1-6}$-alkyl or (20) (1,2,4-oxadiazol-3-yl)$C_{1-6}$-alkyl, wherein the oxadiazolyl group in (19) and (20) is optionally substituted with $C_{1-6}$-alkyl or $C_{3-6}$-cycloalkyl, (21) acyl or (22) a 5-6 membered nitrogen containing ring, optionally substituted with phenyl or $C_{1-6}$-alkyl.

6. A compound of claim 1, wherein

B is NR⁵ and D is —S(=O)—; and

R¹ and R⁵ independently are (1) hydrogen, (2) hydroxy, (3) $C_{1-6}$-alkoxy, (4) $C_{1-6}$-alkyl, (5) $C_{3-6}$-cycloalkyl, (6) $C_{2-6}$-alkenyl or (7) $C_{2-6}$-alkynyl, wherein (4) to (7) are optionally mono- or polysubstituted with halogen and R⁴ is hydrogen, or R⁴ together with R⁵ form a bond, or R⁴ together with R¹ form a bond.

7. A compound of claim 6, wherein R¹ and R⁵ independently are hydrogen or $C_{1-6}$-alkyl.

8. A compound of claim 6, wherein R¹ together with R⁴ form a bond.

9. A compound of claim 6, wherein R⁴ together with R⁵ form a bond.

10. A compound of claim 1, wherein

D—B is —S(=O)(R¹⁰)=N— wherein R¹⁰ is (1) $C_{1-6}$-alkyl, (2) aryl or (3) heteroaryl, wherein (2) and (3) are optionally mono- or polysubstituted with halogen, hydroxy, $C_{1-6}$-alkoxy, aryloxy, arylalkoxy, nitro, amino, $C_{1-6}$-monoalkyl- or dialkylamino, cyano, acyl or $C_{1-6}$-alkoxycarbonyl; and $R^1$ is (1) hydrogen, (2) hydroxy, (3) $C_{1-6}$-alkoxy, (4) $C_{1-6}$-alkyl, (5) $C_{3-6}$-cycloalkyl, (6) $C_{2-6}$-alkenyl or (7) $C_{2-6}$-alkynyl, wherein (4) to (7) are optionally mono- or polysubstituted with halogen and $R^4$ is hydrogen, or $R^4$ together with $R^1$ form a bond.

11. A compound of claim 10, wherein $R^1$ is hydrogen or $C_{1-6}$-alkyl.

12. A compound of claim 10, wherein $R^1$ together with $R^4$ form a bond.

13. A compound of claim 10, wherein $R^{10}$ is $C_{1-6}$-alkyl, phenyl or pyridyl.

14. A pharmaceutical composition comprising a compound of claim 1 together with one or more pharmaceutically acceptable carriers or diluents.

15. The pharmaceutical composition of claim 14 in the form of an oral dosage unit or parenteral dosage unit.

16. A method of treating diseases of the endocrinologic system, comprising administering to a subject in need thereof an effective amount of a compound of claim 1 which acts either as an opener or blocker of $K_{ATP}$-regulated potassium channels.

17. A method of treating diseases of the endocrinologic system, comprising administering to a subject in need thereof an effective amount of a pharmaceutical composition of claim 14, wherein the compound acts either as an opener or blocker of $K_{ATP}$-regulated potassium channels.

18. The method of claim 17, wherein the compound is administered as a dose ranging from 0.05 mg to 1000 mg per day.

19. The method of claim 18, wherein the dose ranges from 0.1 mg to 500 mg per day.

20. The method of claim 19, wherein the dose ranges from 5 mg to 200 mg per day.

21. A compound of formula I

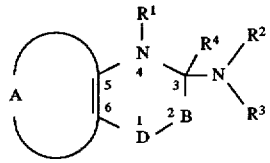

wherein

B is $NR^5$ wherein $R^5$ is (1) hydroxy, (2) $C_{1-6}$-alkoxy, (3) $C_{2-6}$-alkenyl, or (4) $C_{2-6}$-alkynyl, wherein (3) and (4) are optionally mono- or polysubstituted with halogen, or $R^5$ and $R^4$ together form a bond;

D is —S(=O)$_2$—;

$R^1$ is (1) hydrogen, (2) hydroxy, (3) $C_{1-6}$-alkoxy, (4) $C_{1-6}$-alkyl, (5) $C_{3-6}$-cycloalkyl, (6) $C_{2-6}$-alkenyl or (7) $C_{2-6}$-alkynyl, wherein (4) to (7) are optionally mono-or polysubstituted with halogen and $R^4$ is hydrogen or $R^4$ together with $R^5$ form a bond, or $R^1$ together with $R^4$ form a bond;

$R^2$ is (1) hydroxy, (2) $C_{1-6}$-alkoxy, (3) $C_{2-6}$-alkenyl or (4) $C_{2-6}$-alkynyl, wherein (3) and (4) are optionally mono- or polysubstituted with halogen;

$R^3$ is (1) $R^{11}$, (2) —$OR^{11}$, (3) —C(=X)$R^{11}$, (4) —$NR^{11}R^{12}$, (5) bicycloalky, (6) aryl, (7) heteroaryl, (8) arylalkyl or (9) heteroarylalkyl, wherein (5) to (9) are optionally mono- or polysubstituted with halogen, hydroxy, $C_{1-6}$-alkoxy, aryloxy, arylalkoxy, nitro, amino, $C_{1-6}$-monoalkyl- or dialkylamino, cyano, oxo, acyl or $C_{1-6}$-alkoxycarbonyl, or (10) aryl substituted with $C_{1-6}$-alkyl, wherein X is O or S;

$R^{11}$ is (1) hydrogen, (2) $C_{3-6}$-cycloalkyl, (3) ($C_{3-6}$-cycloalkyl)$C_{1-6}$-alkyl, wherein the $C_{3-6}$-cycloalkyl group in (2) and (3) is optionally mono-or polysubstituted with $C_{1-6}$-alkyl, halogen, hydroxy or $C_{1-6}$-alkoxy, (4) a 3–6 membered saturated ring system comprising one or more nitrogen-, oxygen- or sulfur atoms, or (5) straight or branched $C_{1-18}$-alkyl optionally mono- or polysubstituted with halogen, hydroxy, $C_{1-6}$-alkoxy, $C_{1-6}$-alkylthio, $C_{3-6}$-cycloalkyl, aryl, aryloxy, arylalkoxy, nitro, amino, $C_{1-6}$-monoalkyl- or dialkylamino, cyano, oxo, formyl, acyl, carboxy, $C_{1-6}$-alkoxycarbonyl, or carbamoyl;

$R^{12}$ is (1) hydrogen, (2) $C_{1-6}$-alkyl, (3) $C_{2-6}$-alkenyl, or (4) $C_{3-6}$-cycloalkyl which is optionally mono- or polysubstituted with $C_{1-6}$-alkyl, halogen, hydroxy or $C_{1-6}$-alkoxy, or $R^{11}$ and $R^{12}$ together with the nitrogen atom form a 3–12 membered mono- or bicyclic system, in which one or more of the carbon atoms may be exchanged with nitrogen, oxygen or sulfur, each of these ring systems optionally being mono- or polysubstituted with halogen, $C_{1-6}$-alkyl, hydroxy, $C_{1-6}$-alkoxy, $C_{1-6}$-alkoxy-$C_{1-6}$-alkyl, nitro, amino, cyano, trifluoromethyl, $C_{1-6}$-monoalkyl- or dialkylamino, or oxo, or $R^3$ is

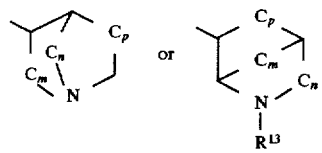

wherein n, m, p independently are 0, 1, 2, or 3 and $R^{13}$ is (1) hydrogen, (2) hydroxy, (3) $C_{1-6}$-alkoxy, (4) $C_{3-6}$-cycloalkyl optionally mono- or polysubstituted with $C_{1-6}$-alkyl, halogen, hydroxy or $C_{1-6}$-alkoxy, (5) $C_{1-6}$-alkyl, (6) $C_{2-6}$-alkenyl, or (7) $C_{2-6}$-alkynyl, wherein (5) to (7) are optionally mono- or polysubstituted with halogen, or $R^2$ and $R^3$ together with the nitrogen atom form a 3–12 membered mono- or bicyclic system, in which one or more of the carbon atoms may be exchanged with nitrogen, oxygen or sulfur, each of these ring systems optionally being mono- or polysubstituted with halogen, $C_{1-6}$-alkyl, hydroxy, $C_{1-6}$-alkoxy, $C_{1-6}$-alkoxy-$C_{1-6}$-alkyl, nitro, amino, cyano, trifluoromethyl, $C_{1-6}$-monoalkyl- or dialkylamino or oxo; and A together with carbon atoms 5 and 6 of formula I form a pyridine ring selected from

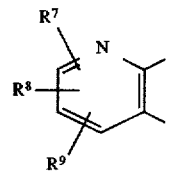

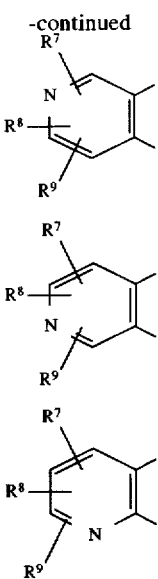

wherein $R^7$, $R^8$, $R^9$ independently are (1) hydrogen, (2) halogen, (3) $C_{1-12}$-alkyl, (4) $C_{3-6}$-cycloalkyl, (5) hydroxy, (6) $C_{1-6}$-alkoxy, (7) $C_{1-6}$-alkoxy-$C_{1-6}$-alkyl, (8) nitro, (9) amino, (10) cyano, (11) cyanomethyl, (12) perhalomethyl, (13) $C_{1-6}$-monoalkyl- or dialkylamino (14) sulfamoyl, (15) -$C_{1-6}$-alkylthio, (16) $C_{1-6}$-alkylsulfonyl, (17) $C_{1-6}$-alkylsulfinyl, (18) $C_{1-6}$-alkylcarbonylamino, (19) arylthio, (20) arylsulfinyl, (21) arylsulfonyl, wherein the aryl group in (19)-(21) is optionally mono- or polysubstituted with $C_{1-6}$-alkyl, halogen, hydroxy or $C_{1-6}$-alkoxy, (22) $C_{1-6}$-alkoxycarbonyl, (23) $C_{1-6}$-alkoxycarbonyl-$C_{1-6}$-alkyl, (24) carbamyl (25) carbamylmethyl, (26) $C_{1-6}$-monoalkyl- or dialkylaminocarbonyl, (27) $C_{1-6}$-monoalkyl- or dialkylaminothiocarbonyl, (28) ureido, (29) $C_{1-6}$-monoalkyl- or dialkylaminocarbonylamino, (30) thioureido, (31) $C_{1-6}$-monoalkyl- or dialkylaminothiocarbonylamino, (32) $C_{1-6}$-monoalkyl-or dialkylaminosulfonyl, (33) carboxy, (34) carboxy—$C_{1-6}$-alkyl, (35) acyl, (36) aryl, (37) arylalkyl, (38) aryloxy, wherein the aryl group in (36) to (38) is optionally mono- or polysubstituted with $C_{1-6}$-alkyl, halogen, hydroxy or $C_{1-6}$-alkoxy, (39) (1,2,4-oxadiazol-5-yl)-$C_{1-6}$-alkyl, (40) (1,2,4-oxadiazol-3-yl)-$C_{1-6}$-alkyl, wherein the oxadiazolyl group in (39) and (40) is optionally substituted with $C_{1-6}$-alkyl or $C_{3-6}$-cycloalkyl, or (41) a 5-6 membered nitrogen containing ring, optionally substituted with phenyl or $C_{1-6}$-alkyl; a pharmaceutical acceptable salt thereof with a pharmaceutically acceptable acid or base; or an optical isomer thereof; or any tautomeric form.

22. A compound of claim 21, wherein $R^3$ is (1) $R^{11}$, (2) —$OR^{11}$, (3) —$NR^{11}R^{12}$ or (4) aryl, the aryl group being optionally substituted with $C_{1-6}$-alkyl, wherein $R^{11}$ is (1) hydrogen, (2) $C_{3-6}$-cycloalkyl, (3) ($C_{3-6}$-cycloalkyl)$C_{1-6}$-alkyl, (4) a 3-6 membered saturated ring system comprising one, two or three nitrogen-, oxygen- or sulfur atoms, or (5) straight or branched $C_{1-18}$-alkyl optionally substituted with halogen, hydroxy, $C_{1-6}$-alkoxy, $C_{1-6}$-alkylthio, $C_{3-6}$-cycloalkyl or aryl, $R^{12}$ is hydrogen, $C_{1-6}$-alkyl or $C_{3-6}$-cycloalkyl, or $R^{11}$ and $R^{12}$ together with the nitrogen atom form a 4-6 membered ring.

23. A compound of claim 21, wherein $R^3$ is secondary $C_{3-6}$-alkyl, tertiary $C_{4-6}$-alkyl, $C_{3-6}$-cycloalkyl or ($C_{3-6}$-cycloalkyl)methyl.

24. A compound of claim 21, wherein $R^7$, $R^8$, $R^9$ independently are (1) hydrogen, (2) halogen, (3) $C_{1-12}$-alkyl, (4) $C_{3-6}$-cycloalkyl, (5) cyano, (6) cyanomethyl, (7) perhalomethyl, (8) sulfamoyl, (9) $C_{1-6}$-alkylthio, (10) $C_{1-6}$-alkylsulfonyl, (11) $C_{1-6}$-alkylsulfinyl, (12) arylthio, (13) arylsulfinyl, (14) arylsulfonyl, wherein the aryl group in (11) to (14) is optionally mono-or polysubstituted with $C_{1-6}$-alkyl, halogen, hydroxy or $C_{1-6}$-alkoxy, (15) $C_{1-6}$-alkoxycarbonyl-$C_{1-6}$-alkyl, (16) carbamylmethyl, (17) carboxy-$C_{1-6}$-alkyl, (18) aryloxy, (19) (1,2,4-oxadiazol-5-yl)-$C_{1-6}$-alkyl or (20) (1,2,4-oxadiazol-3-yl)$C_{1-6}$-alkyl, wherein the oxadiazolyl group in (19) and (20) is optionally substituted with $C_{1-6}$-alkyl or $C_{3-6}$-cycloalkyl, (21) acyl or (22) a 5-6 membered nitrogen containing ring, optionally substituted with phenyl or $C_{1-6}$-alkyl.

25. A compound of claim 21, wherein $R^1$ and $R^5$ independently are (1) hydrogen, (2) hydroxy, (3) $C_{1-6}$-alkoxy, (4) $C_{1-6}$-alkyl, (5) $C_{3-6}$-cycloalkyl, (6) $C_{2-6}$-alkenyl or (7) $C_{2-6}$-alkynyl wherein (4) to (7) are optionally mono- or polysubstituted with halogen and $R^4$ is hydrogen, or $R^4$ together with $R^5$ form a bond, or $R^4$ together with $R^1$ form a bond.

26. A compound of claim 25, wherein $R^1$ and $R^5$ independently are hydrogen or $C_{1-6}$-alkyl.

27. A compound of claim 25, wherein $R^1$ together with $R^4$ form a bond.

28. A compound of claim 25, wherein $R^4$ together with $R^5$ form a bond.

29. A compound of claim 25 which is:

3-Hydrazino-4H-pyrido[4,3-e]-1,2,4-thiadiazine 1,1-dioxide;

3-Benzylamino-4H-pyrido[4,3-e]-1,2,4-thiadiazine 1,1-dioxide;

3-(R)-(1-Phenylethylamino)-4H-pyrido[4,3-e]-1,2,4-thiadiazine 1,1-dioxide;

3-(S)-(1-Phenylethylamino)-4H-pyrido[4,3-e]-1,2,4-thiadiazine 1,1-dioxide;

3-Benzylamino-7-chloro-4H-pyrido[2,3-e]-1,2,4-thiadiazine 1,1-dioxide;

7-Chloro-3-(R)-( 1-phenylethylamino)-4H-pyrido[2,3-e]-1,2,4-thiadiazine 1,1-dioxide;

7-Chloro-3-(S)-( 1'-phenylethylamino)-4H-pyrido[2,3-e]-1,2,4-thiadiazine1, 1-dioxide;

3-Benzylamino-4H-pyrido[2,3-e]-1,2,4-thiadiazine 1,1-dioxide;

3-(R)-(1-Phenylethylamino)-4H-pyrido[2,3-e]-1,2,4-thiadiazine 1,1-dioxide;

3-(S)-(1-Phenylethylamino)-4H-pyrido[2,3-e]-1,2,4-thiadiazine 1,1-dioxide;

3-Allylamino-4H-pyrido[4,3-e]-1,2,4-thiadiazine 1,1-dioxide;

3-Allylamino-7-chloro-4H-pyrido[2,3-e]-1,2,4-thiadiazine 1,1-dioxide;

7—Chloro-3-(2-methoxy-1-methylethyl)amino-4H-pyrido[2,3-e]-1,2,4-thiadiazine 1,1-dioxide;

3-(2-Methoxy-1-methylethyl)amino-4H-pyrido[4,3-e]-1,2,4-thiadiazine 1,1-dioxide;

3-(2-Hydroxy-1-methylethyl)amino-4H-pyrido[4,3-e]-1,2,4-thiadiazine 1,1-dioxide; or 3-Benzylamino-2-methyl-2H-pyrido[4,3-e]-1,2,4-thiadiazine 1,1-dioxide.

30. A pharmaceutical composition comprising a compound of claim 21 together with one or more pharmaceutically acceptable carriers or diluents.

31. The pharmaceutical composition of claim 30 in the form of an oral dosage unit or parenteral dosage unit.

32. A method of treating diseases of the endocrinologic system, comprising administering to a subject in need thereof an effective amount of a compound of claim 21 which acts either as an opener or blocker of $K_{ATP}$-regulated potassium channels.

33. A method of treating diseases of the endocrinologic system, comprising administering to a subject in need thereof an effective amount of a pharmaceutical composition of claim 30, wherein the compound acts either as an opener or blocker of $K_{ATP}$-regulated potassium channels.

34. The method of claim 33, wherein the compound is administered as a dose ranging from 0.05 mg to 1000 mg per day.

35. The method of claim 34, wherein the dose ranges from 0.1 mg to 500 mg per day.

36. The method of claim 35, wherein the dose ranges from 5 mg to 200 mg per day.

37. A compound of formula I

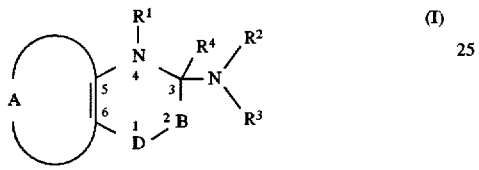

wherein

B is $NR^5$ wherein $R^5$ is (1) hydrogen, (2) hydroxy, (3) $C_{1-6}$-alkoxy, (4) $C_{1-6}$-alkyl, (5) $C_{3-6}$-cycloalkyl, (6) $C_{2-6}$-alkenyl, or (7) $C_{2-6}$-alkynyl, wherein (4) to 7) are optionally mono- or polysubstituted with halogen; or $R^5$ and $R^4$ together form a bond;

D is —S(=O)$_2$—;

$R^1$ is (1) hydrogen, (2) hydroxy, (3) $C_{1-6}$-alkoxy, (4) $C_{1-6}$-alkyl, (5) $C_{3-6}$-cycloalkyl, (6) $C_{2-6}$-alkenyl or (7) $C_{2-6}$-alkynyl, wherein (4) to (7) are optionally mono-or polysubstituted with halogen and $R^4$ is hydrogen or $R^4$ together with $R^5$ form a bond, or $R^1$ together with $R^4$ form a bond;

$R^1$ is (1) hydrogen, (2) hydroxy, (3) $C_{1-6}$-alkoxy, (4) $C_{1-6}$-alkyl, (5) $C_{3-6}$-cycloalkyl, (6) $C_{2-6}$-alkenyl, or (7) $C_{2-6}$-alkynyl, wherein (4) to (7) are optionally mono-or polysubstituted with halogen;

$R^3$ is (1) $R^{11}$, (2) —$OR^{11}$, (3) —$NR^{11}R^{12}$ or (4) aryl, the aryl groups optionally being substituted with $C_{1-6}$-alkyl, wherein $R^{11}$ is (1) hydrogen, (2) $C_{3-6}$-cycloalkyl, (3) ($C_{3-6}$-cycloalkyl)$C_{1-6}$-alkyl, (4) a 3-6 membered saturated ring system comprising one, two or three nitrogen-, oxygen- or sulfur atoms, or (5) straight or branched $C_{1-18}$-alkyl optionally substituted with halogen, hydroxy, $C_{1-6}$-alkoxy, $C_{1-6}$-alkylthio, $C_{3-6}$-cycloalkyl or aryl, $R^{12}$ is hydrogen, $C_{1-6}$-alkyl or $C_{3-6}$-cycloalkyl, or $R^{11}$ and $R^{12}$ together with the nitrogen atom form a 4-6 membered ring; and A together with carbon atoms 5 and 6 of formula I form a pyridine ring selected from

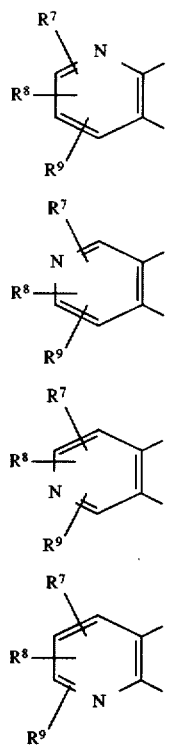

wherein $R^7$, $R^8$, $R^9$ independently are (1) hydrogen, (2) halogen, (3) $C_{1-12}$-alkyl, (4) $C_{3-6}$-cycloalkyl, (5) hydroxy, (6) $C_{1-6}$-alkoxy, (7) $C_{1-6}$-alkoxy-$C_{1-6}$-alkyl, (8) nitro, (9) amino, (10) cyano, (11) cyanomethyl, (12) perhalomethyl, (13) $C_{1-6}$-monoalkyl- or dialkylamino (14) sulfamoyl, (15) $C_{1-6}$-alkylthio, (16) $C_{1-6}$-alkylsulfonyl, (17) $C_{1-6}$-alkylsulfinyl, (18) $C_{1-6}$-alkylcarbonylamino, (19) arylthio, (20) arylsulfinyl, (21) arylsulfonyl, wherein the aryl group in (19)-(21) is optionally mono- or polysubstituted with $C_{1-6}$-alkyl, halogen, hydroxy or $C_{1-6}$-alkoxy, (22) $C_{1-6}$-alkoxycarbonyl, (23) $C_{1-6}$-alkoxycarbonyl—$C_{1-6}$-alkyl, (24) carbamyl, (25) carbamylmethyl, (26) $C_{1-6}$-monoalkyl- or dialkylaminocarbonyl, (27) $C_{1-6}$-monoalkyl- or dialkylaminothiocarbonyl, (28) ureido, (29) $C_{1-6}$-monoalkyl- or dialkylaminocarbonylamino, (30) thioureido, (31) $C_{1-6}$-monoalkyl-or dialkylaminothiocarbonylamino, (32) $C_{1-6}$-monoalkyl-or dialkylaminosulfonyl, (33) carboxy, (34) carboxy-$C_{1-6}$-alkyl, (35) acyl, (36) aryl, (37) arylalkyl, (38) aryloxy, wherein the aryl group in (36) to (38) is optionally mono- or polysubstituted with $C_{1-6}$-alkyl, halogen, hydroxy or $C_{1-6}$-alkoxy, (39) (1,2,4-oxadiazol-5-yl)-$C_{1-6}$-alkyl, (40) (1,2,4-oxadiazol-3-yl)-$C_{1-6}$-alkyl, wherein the oxadiazolyl group in (39) and (40) is optionally substituted with $C_{1-6}$-alkyl or $C_{3-6}$-cycloalkyl, or (41) a 5-6 membered nitrogen containing ring, optionally substituted with phenyl or $C_{1-6}$-alkyl; or a pharmaceutical acceptable salt thereof with a pharmaceutically acceptable acid or base; or an optical isomer thereof; or any tautomeric form provided that when B represents $NR^5$, D represents $SO_2$ and $R^2$ is hydrogen, $C_{1-6}$-alkyl or $C_{3-6}$-cycloalkyl, then $R^3$ is not hydrogen, $C_{1-6}$-alkyl, $C_{3-6}$-cycloalkyl, ($C_{3-6}$-cycloalkyl)$C_{1-6}$-alkyl, pyrrolidine, piperidine, piperazine, morpholine, thiomorpholine or benzyl.

38. A compound of claim 37, wherein $R^2$ is hydrogen or $C_{1-6}$-alkyl.

39. A compound of claim 37, wherein $R^3$ is secondary $C_{3-6}$-alkyl, tertiary $C_{4-6}$-alkyl, $C_{3-6}$-cycloalkyl or ($C_{3-6}$-cycloalkyl)methyl.

40. A compound of claim 37, wherein $R^7$, $R^8$, $R^9$ independently are (1) hydrogen, (2) halogen, (3) $C_{1-12}$-alkyl, (4) $C_{3-6}$-cycloalkyl, (5) cyano, (6) cyanomethyl, (7) perhalomethyl (8) sulfamoyl, (9) $C_{1-6}$-alkylthio, (10) $C_{1-6}$-alkylsulfonyl, (11) $C_{1-6}$-alkylsulfinyl, (12) (13) arylsulfinyl, (14) arylsulfonyl, wherein the aryl group in (11) to (14) is optionally mono-or polysubstituted with $C_{1-6}$-alkyl, halogen, hydroxy or $C_{1-6}$-alkoxy, (15) $C_{1-6}$-alkoxycarbonyl-$C_{1-6}$-alkyl, (16) carbamylmethyl, (17) carboxy-$C_{1-6}$-alkyl, (18) aryloxy, (19) (1,2,4-oxadiazol-5-yl)- or (20) (1,2,4-oxadiazol-3-yl)$C_{1-6}$-alkyl, wherein the oxadiazolyl group in (19) and (20) is optionally substituted with $C_{1-6}$-alkyl or $C_{3-6}$-cycloalkyl, (21) acyl or (22) a 5-6 membered nitrogen containing ring, optionally substituted with phenyl or $C_{1-6}$-alkyl.

41. A compound of claim 37, wherein $R^1$ and $R^5$ independently are (1) hydrogen, (2) hydroxy, (3) $C_{1-6}$-alkoxy, (4) $C_{1-6}$-alkyl, (5) $C_{3-6}$-cycloalkyl, (6) $C_{2-6}$-alkenyl or (7) $C_{2-6}$-alkynyl wherein (4) to (7) are optionally mono- or polysubstituted with halogen and $R^4$ is hydrogen; or $R^4$ together with $R^5$ form a bond; or $R^4$ together with $R^1$ form a bond.

42. A compound of claim 41, wherein $R^1$ and $R^5$ independently are hydrogen or $C_{1-6}$-alkyl.

43. A compound of claim 41, wherein $R^1$ together with $R^4$ form a bond.

44. A compound of claim 41, wherein $R^4$ together with $R^5$ form a bond.

45. A compound of claim 37 which is:

3-Hydrazino-4H-pyrido[4,3-e]-1,2,4-thiadiazine 1,1-dioxide;

3-Benzylamino-4H-pyrido[4,3-e]-1,2,4-thiadiazine 1,1-dioxide;

3-(R)-(1-Phenylethylamino)-4H-pyrido[4,3-e]-1,2,4-thiadiazine 1,1-dioxide;

3-(S)-(1-Phenylethylamino)-4H-pyrido [4,3-e]-1,2,4-thiadiazine 1,1-dioxide;

3-Benzylamino-7-chloro-4H-pyrido [2,3-e] -1,2,4-thiadiazine 1,1-dioxide;

7-Chloro-3-(R)-(1-phenylethylamino)-4H-pyrido[2,3-e]-1,2,4-thiadiazine 1,1 -dioxide;

7-Chloro-3-(S)-(1'-phenylethylamino)-4H-pyrido[2,3-e]-1,2,4-thiadiazine1, 1-dioxide;

3-Benzylamino-4H-pyrido[2,3-e]-1,2,4-thiadiazine 1,1-dioxide;

3-(R)-(1-Phenylethylamino)-4H-pyrido[2,3-e]-1,2,4-thiadiazine 1,1-dioxide;

3-(S)-(1-Phenylethylamino)-4H-pyrido[2,3-e]-1,2,4-thiadiazine 1,1-dioxide;

3-Allylamino-4H-pyrido[4,3-e]-1,2,4-thiadiazine 1,1-dioxide;

3-Allylamino-7-chloro-4H-pyrido[2,3-e]-1,2,4-thiadiazine 1,1-dioxide;

7-Chloro-3-(2-methoxy-1-methylethyl)amino-4H-pyrido [2,3-e]-1,2,4-thiadiazine 1,1-dioxide;

3-(2-Methoxy-1-methylethyl)amino-4H-pyrido[4,3-e]-1,2,4-thiadiazine 1,1-dioxide;

3-(2-Hydroxy-1-methylethyl)amino-4H-pyrido[4,3-e]-1,2,4-thiadiazine 1,1-dioxide; or 3-Benzylamino-2-methyl-2H-pyrido[4,3-e]-1,2,4-thiadiazine 1,1-dioxide.

46. A pharmaceutical composition comprising a compound of claim 37 together with one or more pharmaceutically acceptable carriers or diluents.

47. The pharmaceutical composition of claim 46 in the form of an oral dosage unit or parenteral dosage unit.

48. A method of treating diseases of the endocrinologic system, comprising administering to a subject in need thereof an effective amount of a compound of claim 37 which acts either as an opener or blocker of $K_{ATP}$-regulated potassium channels.

49. A method of treating diseases of the endocrinologic system, comprising administering to a subject in need thereof an effective amount of a pharmaceutical composition of claim 46, wherein the compound acts either as an opener or blocker of $K_{ATP}$-regulated potassium channels.

50. The method of claim 49, wherein the compound is administered as a dose ranging from 0.05 mg to 1000 mg per day.

51. The method of claim 50, wherein the dose ranges from 0.1 mg to 500 mg per day.

52. The method of claim 51, wherein the dose ranges from 5 mg to 200 mg per day.

* * * * *